US012472063B2

(12) United States Patent
Dierckx et al.

(10) Patent No.: US 12,472,063 B2
(45) Date of Patent: Nov. 18, 2025

(54) METHOD AND APPARATUS FOR TREATING HYPERINFLATION AND ASSOCIATED COMPLICATIONS IN LUNG REGIONS

(71) Applicants: Materialise N.V., Leuven (BE); Fluidda NV, Kontich (BE)

(72) Inventors: Antoon Dierckx, Heverlee (BE); Ben Bekaert, Bertem (BE); Jan De Backer, Kontich (BE)

(73) Assignees: Materialise N.V., Leuven (BE); Fluidda NV, Kontich (BE)

( * ) Notice: Subject to any disclaimer, the term of this patent is extended or adjusted under 35 U.S.C. 154(b) by 0 days.

(21) Appl. No.: 19/214,919

(22) Filed: May 21, 2025

(65) Prior Publication Data

US 2025/0281296 A1 Sep. 11, 2025

Related U.S. Application Data

(63) Continuation of application No. PCT/US2023/079877, filed on Nov. 15, 2023.

(60) Provisional application No. 63/428,338, filed on Nov. 28, 2022.

(51) Int. Cl.

| | |
|---|---|
| ***A61F 2/04*** | (2013.01) |
| ***A61F 2/24*** | (2006.01) |
| ***A61L 31/10*** | (2006.01) |

(52) U.S. Cl.

CPC ............ *A61F 2/2476* (2020.05); *A61L 31/10* (2013.01); *A61F 2002/043* (2013.01); *A61F 2210/0076* (2013.01)

(58) Field of Classification Search

CPC .... A61F 2/04; A61F 2002/043; A61F 2/2476; A61F 2/2412; A61M 16/208; A61M 2210/1035

See application file for complete search history.

(56) References Cited

U.S. PATENT DOCUMENTS

| | | | | |
|---|---|---|---|---|
| 5,332,403 A * | 7/1994 | Kolff | A61M 60/896 | 600/16 |
| 6,120,534 A * | 9/2000 | Ruiz | A61F 2/86 | 623/1.3 |
| 7,771,472 B2 * | 8/2010 | Hendricksen | A61B 17/12104 | 128/207.15 |
| 7,867,274 B2 * | 1/2011 | Hill | A61F 2/2475 | 623/2.12 |
| 11,224,503 B2 * | 1/2022 | Karavany | A61F 2/966 | |

(Continued)

FOREIGN PATENT DOCUMENTS

| | | | | |
|---|---|---|---|---|
| CN | 114052991 A | 2/2022 | | |
| DE | 102020006503 A1 | 4/2022 | | |
| WO | WO-2021150872 A1 * | 7/2021 | | A61F 2/2476 |

OTHER PUBLICATIONS

PCT International Search Report and Written Opinion of International Patent Application PCT/US2023/079877, mailed Feb. 21, 2024, 11 pages, International Searching Authority (EPO).

*Primary Examiner* — Seema Mathew

(74) *Attorney, Agent, or Firm* — Dinsmore & Shohl LLP

(57) ABSTRACT

Certain embodiments provide a method for controlling airflow in a lung of a respiratory system of a patient. The method generally includes placing a device in an airway passage, wherein the device comprises: an outer wall and an inner wall defining a lumen from a proximal end to a distal end of the device and changing a volume of the lumen over time.

19 Claims, 14 Drawing Sheets

(56) References Cited

U.S. PATENT DOCUMENTS

| | | | | |
|---|---|---|---|---|
| 11,717,425 | B2 * | 8/2023 | Bruckheimer | A61F 2/06 623/1.14 |
| 11,771,434 | B2 * | 10/2023 | Bellomo | A61F 2/90 606/191 |
| 2006/0020347 | A1 * | 1/2006 | Barrett | A61F 2/2476 623/23.65 |
| 2006/0076023 | A1 | 4/2006 | Rapacki et al. | |
| 2006/0107956 | A1 * | 5/2006 | Hendricksen | A61F 2/04 128/207.14 |
| 2011/0226238 | A1 * | 9/2011 | Barrett | A61B 17/12172 128/200.24 |
| 2021/0161643 | A1 * | 6/2021 | Totten | A61F 2/2436 |
| 2021/0169634 | A1 * | 6/2021 | Karavany | A61F 2/915 |
| 2021/0386959 | A1 * | 12/2021 | Oddo | A61M 16/147 |
| 2022/0022881 | A1 * | 1/2022 | Celermajer | A61F 2/064 |
| 2022/0039938 | A1 * | 2/2022 | Karavany | A61M 60/861 |
| 2022/0054261 | A1 * | 2/2022 | Argento | A61F 2/95 |
| 2022/0211481 | A1 * | 7/2022 | Totten | A61F 2/2476 |
| 2022/0233309 | A1 * | 7/2022 | Yoganathan | A61F 2/2418 |
| 2022/0241063 | A1 * | 8/2022 | Karavany | A61F 2/07 |
| 2023/0129792 | A1 * | 4/2023 | Hartman | A61B 18/14 623/2.18 |

* cited by examiner

METHOD AND APPARATUS FOR TREATING HYPERINFLATION AND ASSOCIATED COMPLICATIONS IN LUNG REGIONS

CROSS-REFERENCE TO RELATED APPLICATIONS

This Application is a continuation of International Application No. PCT/US2023/079877, filed on Nov. 15, 2023, which claims the benefit of and priority to U.S. Provisional Patent Application No. 63/428,338, filed on Nov. 28, 2022, the entire disclosures of both of which are hereby incorporated by reference.

BACKGROUND

Field of the Invention

This disclosure relates to a field of lung treatment, and more specifically, to treatment of respiratory conditions. Aspects of this disclosure relate to methods, devices, and systems which allow for treating hyperinflation and its related complications.

Description of the Related Technology

Chronic Obstructive Pulmonary Disease (COPD) is the third leading cause of death worldwide. COPD is an obstructive respiratory disease that is characterized by persistent and progressive airflow limitation in the lungs. COPD is an umbrella term given to a group of chronic lung diseases including emphysema and chronic bronchitis.

COPD (type emphysema) results in a reduction of the lung tissue's elasticity, leading to a reduced natural elastic recoil, which triggers the pressure in the airways to drop, and the distal airways to collapse when a patient exhales. When the affected airways collapse, oxygen ($O_2$)-poor air is trapped and cannot be exhaled, nor can the $O_2$-poor air be replaced with $O_2$-rich air when the patient inhales. This trapped air leads to hyperinflation, which is associated with reduced ventilation and a decrease in oxygen uptake capacity.

A majority of patients suffering from emphysema and/or associated hyperinflation receive pharmacologic treatments such as bronchodilators, non-invasive ventilation (NIV) support, and/or physiotherapy to learn techniques like pursed-lip-breathing to temporarily reduce the risk of airways collapsing. However, for patients with severe COPD, these treatments are not (sufficiently) effective. In particular, a severe COPD patient may be treated with surgical or endobronchial lung volume reduction treatments only where the patient meets strict inclusion criteria. Aside from the fact that not every severe COPD patient can receive surgical or endobronchial lung volume reduction as a treatment, these treatments are also associated with high rates of complications like pneumothorax (e.g., a collapsed lung).

NIV refers to the delivery of positive pressure through a noninvasive interface (e.g., a nasal mask, face mask, nasal plugs, etc.), rather than an invasive interface (e.g., endotracheal tube, tracheostomy, etc.). NIV may lead to an increase in ventilation (e.g., higher ventilation/perfusion ratio). Additional details of NIV and its advantages are disclosed in International Patent Application No. PCT/US2016/064181, filed on Nov. 30, 2016, and titled "Method and apparatus for improved airflow distribution," which is hereby incorporated by reference herein in its entirety. However, although an increase in ventilation may be recorded after NIV treatment, NIV may not reduce hyperinflation. Instead, the positive effect of administering NIV, and those results observed thereafter, are believed to relate mostly to the temporary offloading of the inspiratory muscles. Furthermore, this treatment is generally applied to the entirety of the respiratory system and may not be used as a treatment on a local and/or regional level. Thus, NIV treatment may not account for heterogeneity of the disease.

Pursed lips breathing is a technique that allows patients to control their oxygenation and ventilation. The technique requires a patient to inhale through the nose and exhale through the mouth at a slow controlled pace. As the patient slowly breathes out while pursing the lips, the outlet area through which air flows from the respiratory system into the environment is reduced, resulting in increased resistance to outflowing air. As a result of this increased resistance to outflowing air, the pressure inside the airways during exhalation may increase. This positive pressure is known as positive end expiratory pressure (PEEP). The created PEEP may help to prevent airways affected by emphysema from collapsing. However, this technique may not be performed continuously, and the effects are rather limited and small. Additionally, the intervention may not be administered at a regional and/or local level.

Endobronchial lung volume reduction can be achieved by placing one-way endobronchial valves (EBV) in certain airways. EBV valves are removable, one-way valves that reduce lung hyperinflation by allowing trapped air to escape. These one-way valves result in the targeted regions where the implants/stents/valves are placed becoming non-functional and/or deflating over time, eventually leading to collapse of that targeted region. This is an aggressive intervention as it results in full collapse and necrosis of affected regions, thereby limiting optimization for potential healthy ventilation/perfusion matching in areas that would collapse otherwise.

Use of EBV valves, stents, and/or implants may also lead to other complications such as mucus plugs (e.g., mucus that accumulates in the airways and blocks airflow) and migration of the stents, among others. Further, in some cases, placement of EBV valves may be associated with pneumothorax as a complication which may cause patient discomfort, prolonged hospitalization, interventional procedures, and/or overall deterioration of the patient's health.

SUMMARY

Certain embodiments provide a method for controlling airflow in a lung of a respiratory system of a patient. The method generally includes placing a device in an airway passage, wherein the device comprises: an outer wall; and an inner wall defining a lumen from a proximal end to a distal end of the device; and changing a volume of the lumen over time.

Certain embodiments provide a pulmonary implant device. The pulmonary implant device generally includes an outer wall; an inner wall defining a lumen from a proximal end to a distal end of the pulmonary implant device; and a one-way valve positioned within the lumen, the one-way valve configured to permit airflow in a first direction through the one-way valve and prevent airflow in a second direction through the one-way valve, wherein, in at least a first configuration of the pulmonary implant device, there is a gap between at least a portion of the one-way valve and the inner wall, the gap configured to permit airflow in both the first direction and the second direction through the lumen from the proximal end to the distal end of the pulmonary implant device.

DETAILED DESCRIPTION

Figure 1:
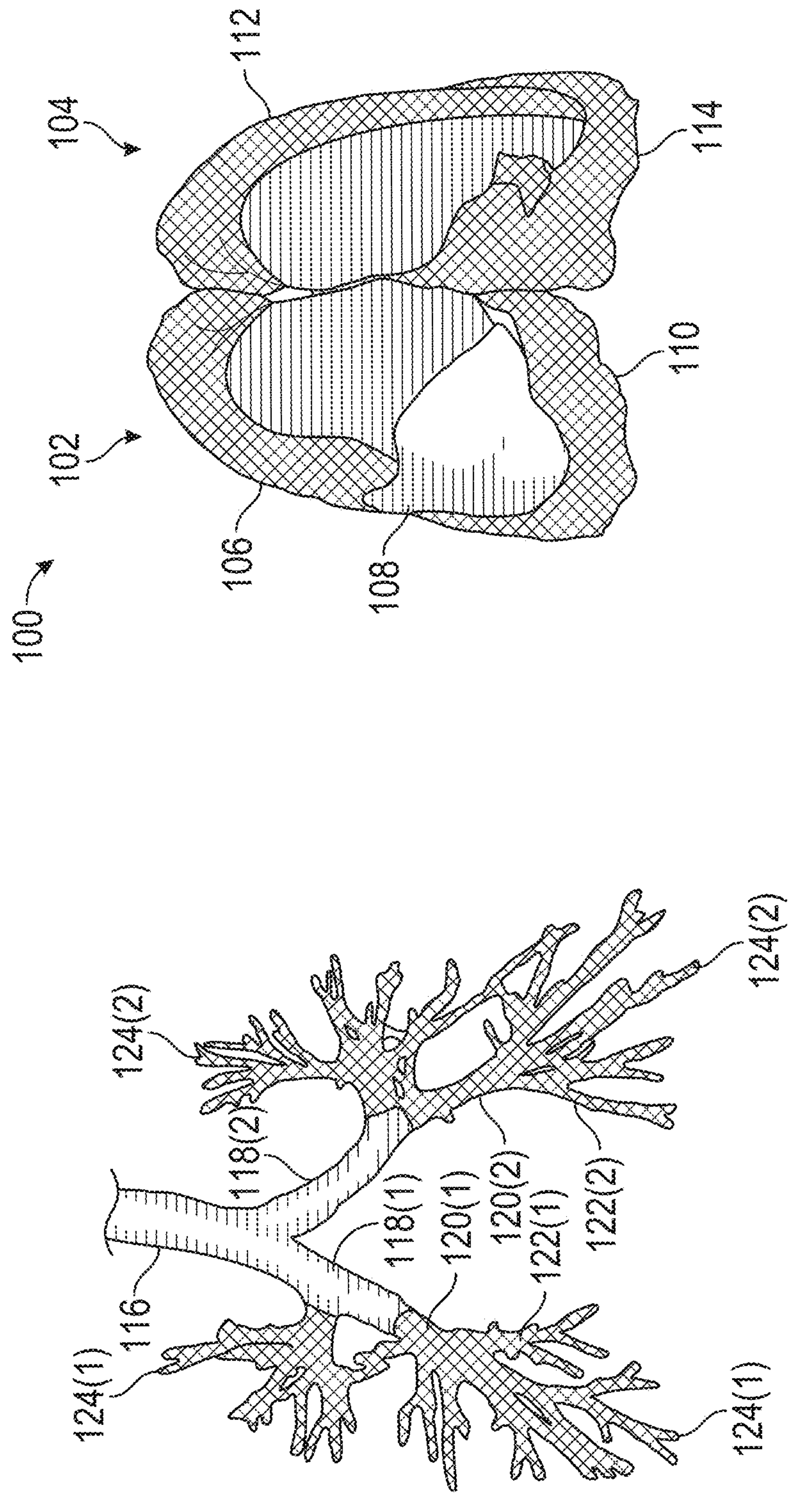
FIG. 1 is an example of a healthy respiratory system.

Certain embodiments disclosed herein relate to methods, devices, and systems used for the treatment of patients suffering from respiratory conditions. These conditions may include COPD, Idiopathic Pulmonary Fibrosis (IPF), asthma, cystic fibrosis (CF), pneumothorax, hyperinflation, and/or the like. A person skilled in the art will recognize that the methods, devices, and systems described herein may be applicable to other conditions as well.

As used herein, the term "targeted lung region(s)" encompasses a wide variety of pulmonary regions. For example, "targeted lung region(s)" may be used to refer to one or more of "lung lobe(s)," "lung region(s)," "lung segment(s)," "lung sub-segment," and/or the like, that are targeted and/or selected for treatment.

As used herein, the term "airway implant" encompasses a wide variety of devices. For example, "airway implant" may be used to refer to one or more of "implant(s)," "stent(s)," "endobronchial stent(s)," "endobronchial device(s)," "endobronchial implant(s)," and/or the like.

As used herein, the term "fluid" may refer to any substance that flows. For example, the term "fluid," may be used to refer to one or more of "air," "liquid," "mucus," "secretions," "gaseous substances," and/or the like.

Unless otherwise mentioned, the term "airway(s),", as used herein, may refer to one or more of "branches of the lung," "branches of a lung region(s)," "branches of selected lung lobe(s)," "branches of a selected lung region(s)," "selected airway(s)," "selected airway channel(s)," "airway channel(s)," "branches of a selected lung segment(s)," and/or the like.

As used herein, reference to an element/component as a "plurality" may not be intended to mean only "more than one," unless specifically so stated, but rather "one or more."

As used herein, the term "operator" refers to a person executing a method or method steps, and/or operating device(s) and/or system(s), described herein. Unless otherwise mentioned, the "operator" may refer to one or more of a "user," "medical professional," "clinician," "a non-medical professional," (e.g., such as a technician, engineer, or a trained employee), and/or the like.

Certain embodiments disclosed herein relate to methods, devices, and systems that are used for creating and/or assisting in creating positive end expiratory pressure (PEEP) in at least one targeted lung region to provide a heterogenic, localized solution that targets the actual condition of a patient.

Certain embodiments disclosed herein relate to methods, devices, and systems that are used for treatment of hyperinflation in at least one targeted lung region. The lung region(s) may be selected based on disease progression and/or during treatment planning.

Certain embodiments disclosed herein relate to methods, devices, and systems that are used for preventing pneumothorax in at least one targeted lung region and/or at least one selected airway.

Certain embodiments disclosed herein relate to methods, devices, and systems that are used for preventing mucus plugging in at least one targeted lung region.

Certain embodiments disclosed herein relate to devices that are used for treatment of hyperinflation and/or associated complications.

In sum, certain embodiments described herein introduce a pulmonary implant device (subsequently referred to herein as a "device") configured to control airflow in a lung of a respiratory system of a patient. For example, the device described herein includes an outer wall and an inner wall defining a lumen from a proximal end to a distal end of the device. A volume of the lumen may be designed to change over time (e.g. narrow over time) to introduce increased resistance to airflow, thereby resulting in positive pressure in airways distal to a region of the lung where the device is placed, at the time of exhalation. This is commonly referred to as PEEP. PEEP prevents airways and/or alveoli distal to the device from collapsing, thereby facilitating deflation of targeted lung region(s) and/or lobe(s) while further improving regional ventilation/perfusion. Unlike bronchoscopic lung volume reduction (BLVR) used alongside endobronchial valve (EBV) treatments previously described, devices, methods, and systems described herein restore the ventilation and gaseous exchange in targeted region(s) of the lung.

Further, the devices, methods, and systems described herein may be used in treatment of patients suffering from severe hyperinflation, for whom today, a limited number of treatment options (or, in some cases, no treatment options) exist. The described devices, methods, and systems also aim to reduce other complications, such as risk of pneumothorax (e.g., which is currently a complication of the BLVR treatment). As will become evident from the description below, the risk is reduced due to the ability of the described devices to partially block the airflow to one or more targeted regions of the lung, as opposed to complete blockage. This may result in a smaller air volume that may be redistributed to neighboring lung regions, thereby making it easier for the respiratory system to adapt to new changes.

Certain embodiments described herein provide methods for designing such device(s) for placement in one or more airway passages of a patient, determining a degree of lumen narrowing for the device(s) over time, determining a number of devices to be designed and positioned within airway passage(s) of a patient, and determining locations (e.g., targeted lung region(s) and/or airway passage(s)) for device placement.

Turning now to FIG. 1, an anterior view of a normal, healthy respiratory system 100 is illustrated. On the left side of FIG. 1, airway passages through the lungs 102 and 104 are shown, while on the right side of FIG. 1, lungs 102 and 104 themselves are shown. Respiratory system 100 includes a right lung 102 and a left lung 104. Right lung 102 includes a right lung upper lobe 106, a right lung middle lobe 108, and a right lung lower lobe 110. Left lung 104 has only two lobes, for example, the upper lobe 112 and the lower lobe 114.

On the left side of FIG. 1, the airway passages of respiratory system 100 are shown. These airway passages pass through the lung tissue of right lung 102 and left lung 104. The airway passages include a trachea 116 (also commonly referred to as a windpipe). Trachea 116 extends from the chest area towards a head of a patient and allows air to be inhaled and exhaled through the patient's mouth and nose. As trachea 116 extends downward, trachea 116 divides into two branches 118. These two branches 118(1) and 118(2) are commonly referred to as bronchi. As illustrated, there is a main (right) bronchus 118(1) which extends downward from trachea 116 and to the left side of the drawing (because the view is from the anterior, or front, of the body). The main (right) bronchus 118(1) provides an airway passage into right lung 102. There is also a main (left) bronchus 118(2) on the left side of trachea 116 (right side in the drawing) which leads into left lung 104.

The airway passages of respiratory system 100 grow progressively smaller as they branch out within lungs 102 and 104 until the airway passages ultimately become microscopic in size. Main (right) bronchus 118(2) and main (left) bronchus 118(2) each branch into lobar bronchi 120 (e.g., right lobar bronchus 120(1) and left lobar bronchus 120(2)). Although each main bronchus 118(1), 118(2) branches into two or three lobar bronchus 120(1), 120(2), respectively, only one is marked in each branch in FIG. 1. Right lobar bronchus 120(1) and left lobar bronchus 120(2), in turn, narrow into right segmental bronchus 122(1) and left segmental bronchus 122(2) (collectively referred to as "segmental bronchi 122") which carry air further down the air passages to bronchioles 124(1), 124(2) (collectively referred to as "bronchioles 124"). Bronchioles 124 terminate as terminating bronchioles.

At the end of bronchioles 124, there exists clusters of microscopic air sacs called alveoli (not illustrated in FIG. 1). The alveoli are where the lungs and the blood exchange oxygen and carbon dioxide (e.g., a waste produce of metabolism) during the process of breathing in and breathing out. For example, in the alveoli, oxygen from the air is absorbed into the blood. Carbon dioxide travels from the blood to the alveoli, where it can be exhaled upward through the airway passages of the lungs.

In patients with emphysema, the alveoli may become damaged. For example, over time, the inner walls of the air sacs may weaken and rupture, thereby creating larger air spaces instead of many small ones.

Figure 2:
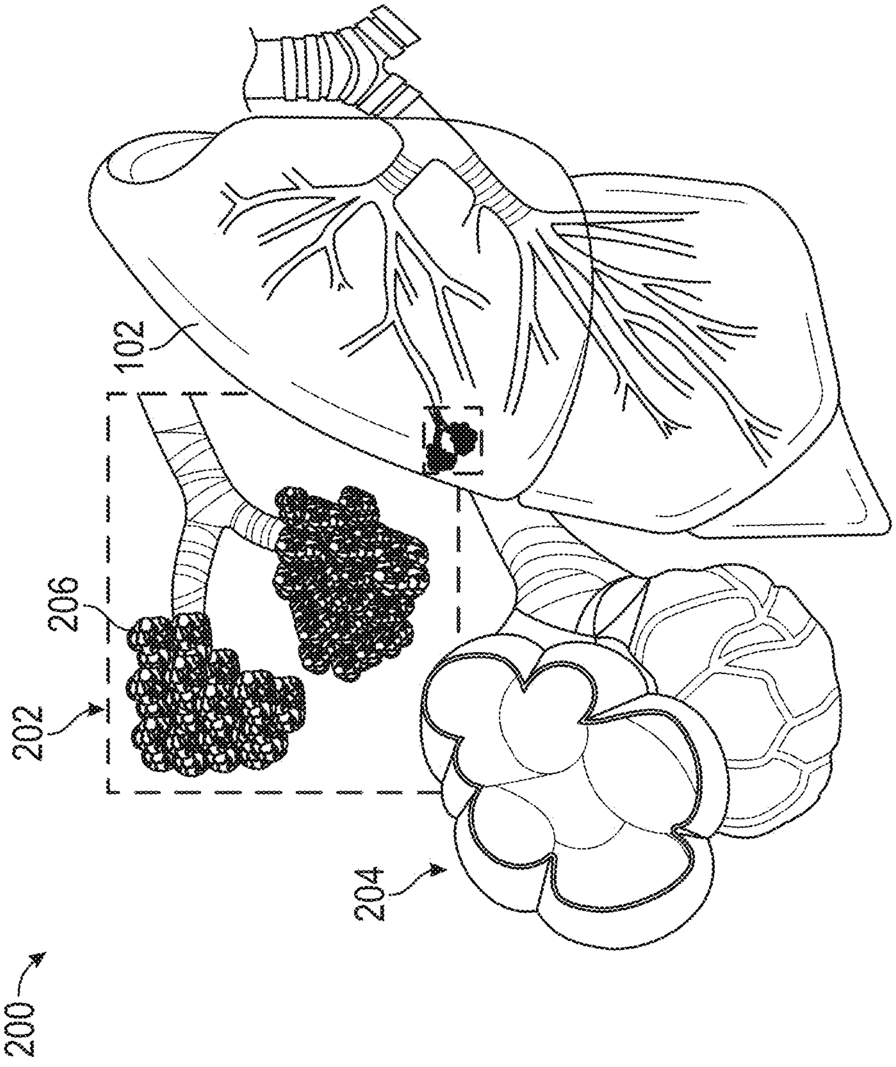
FIG. 2 is an example respiratory system having damaged alveoli.

FIG. 2 is an example respiratory system 200 having damaged alveoli. As illustrated for right lung 102 in FIG. 2, normal alveoli 202 are organized into bunches, where each bunch is grouped into what is called an alveolar sac 206. Each alveolus (e.g., singular of alveoli) is cup-shaped with very thin walls. Further, each alveolus is surrounded by networks of blood vessels, referred to as capillaries, that also have thin walls.

As a patient breathes in air, the alveoli stretch, drawing oxygen in and transporting this oxygen to the blood. At the same time, carbon dioxide waste moves into the air sacs from the capillaries. This process is commonly referred to as gas exchange. Additionally, when a patient exhales, the alveoli shrink, forcing carbon dioxide out of the body through various airways.

When emphysema develops, however, the alveoli and distal airway branches lose their elasticity and shape. For example, as illustrated in FIG. 2, for damaged alveoli 204, walls between many of the alveolar sacs 206 are damaged, thereby creating a lesser number of larger air spaces, instead of many small ones. This reduces the surface area of the lungs and, in turn, the amount of oxygen that reaches the bloodstream. Accordingly, when a patient exhales, the damaged alveoli 204 may not work properly, and old air may become trapped, leaving little to no room for fresh, oxygen-rich air to enter.

Due the lungs' inability to properly push out air when a patient exhales, the lungs may become hyperinflated. In particular, hyperinflated lungs are larger-than-normal lungs as a result of trapped air. Functionally, hyperinflation implies an increased ratio of residual volume (RV) to total lung capacity (TLC), with a shift of tidal breathing at the expense of inspiratory capacity. Inspiratory capacity refers to the maximum volume of air that can be inspired after reaching the end of a normal, quiet expiration.

Further, in some cases, damaged alveoli 204 may not be able support bronchial tubes which carry air into the alveoli. As such, the bronchial tubes may collapse and cause an "obstruction" (e.g., a blockage), which further traps air inside the lungs. Accordingly, collapsed bronchial tubes may also lead to hyperinflation of the lungs.

Figure 3:
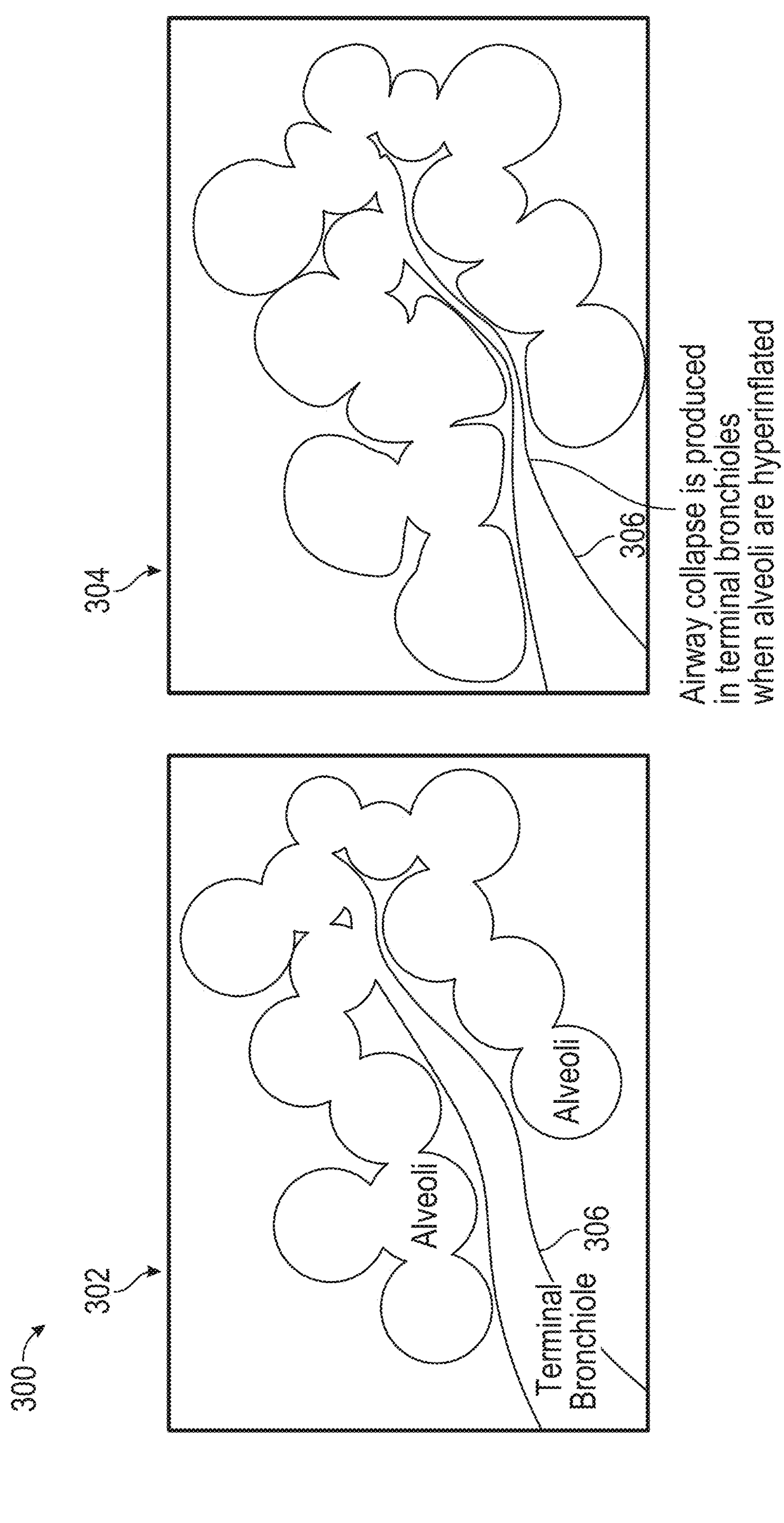
FIG. 3 is an example respiratory system with a collapsed airway.

FIG. 3 is an example respiratory system 300 with a collapsed airway. In particular, as illustrated in FIG. 3, in patients with normal alveoli (e.g., shown at 302), the alveoli may be able to support airways 306 (e.g., such as bronchioles, which may include a terminal bronchiole) carrying oxygen towards the alveoli for gas exchange. On the other hand, in patients with damaged alveoli (e.g., shown at 304), airway 306 collapse(s) may result as a consequence of the alveoli losing their elasticity and becoming hyperinflated.

In accordance with certain embodiments of the present disclosure, a pulmonary implant device may be positioned within at least one airway of a targeted lung region, such as airway 306 illustrated in FIG. 3, to introduce increased resistance to airflow. The increased resistance to airflow may create PEEP in airways distal to the device as compared to airways proximal to the device. This PEEP may help to prevent airways and/or alveoli distal to the device from collapsing during exhalation by a patient, thereby enabling air to flow out of alveoli and through the airways, such that this air is able to be replaced with fresh air, for example, when the patient subsequently inhales.

According to an embodiment, the device may be a stent or stent-like device that is generally cylindrical in shape. The device may be hollowed such that the device includes an outer wall or surface and an inner wall or surface. The outer wall is the wall that faces the airway and/or the region. The thickness of the device as formed between the outer wall and inner wall may be suitable for providing sufficient strength to the hollowed device. In certain embodiments, the outer wall sits flush with the surrounding tissue. The inner wall is the wall that faces away from the airway and/or the region towards the hollow airway channel. Both the outer and inner walls may be further divided into sub-walls (also referred to herein as sub-surfaces). The outer wall, inner wall, and sub-walls may be designed separately or together in accordance with a requirement. For example, the outer wall may be designed to match a shape of an airway where the device is placed, while the inner wall (or sub-surfaces) may be designed to have an inner constriction that creates an intended level of PEEP (e.g., based on a pre-procedural analysis, described in more detail below).

In certain embodiments, the inner wall defines a lumen from a proximal end to a distal end of the device (e.g., the hollowed area of the device). According to embodiments described herein, the cross-sectional diameter of the lumen may become progressively narrower as it proceeds inward towards a center portion of the length of the lumen.

For example, in certain embodiments, the device may be designed such that the lumen of the device is open along the entire length of the device (e.g., prior to making any changes to the volume of the lumen), thereby allowing air to pass through the device from a proximal end of the device to a distal end of the device. In other words, airflow may be bidirectional through the lumen of the device (e.g., unlike currently available EBVs that only allow air to flow in one direction). Additionally, the lumen of the device may have a larger diameter near the open ends of the device and gradually narrow towards its minimal average cross-sectional diameter located at one or more point(s) in between both ends of the device. The diameter of the narrowest cross-section may be determined such that the device creates a positive pressure that is sufficient to avoid collapse of the airways that are distal to the device while the patient exhales. The design of the device may also depend on one or more patient-specific parameters, as described below, such as the length of the airway branch, the minimal, maximal, and/or average diameter of the targeted airway branch, etc. Additional details regarding determining a narrowest-cross section of the device is provided below with reference to FIG. 12.

Figure 4B:
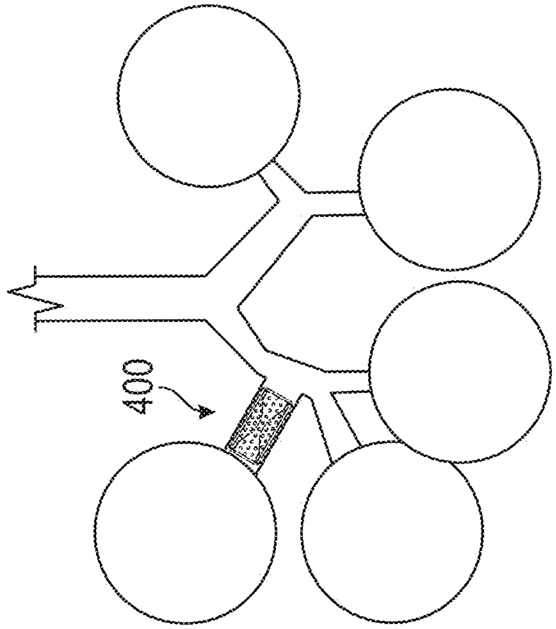
FIGS. 4A and 4B illustrate an example pulmonary implant device with a narrowed lumen to control airflow, in accordance with certain embodiments of the present disclosure.
Figure 4A:
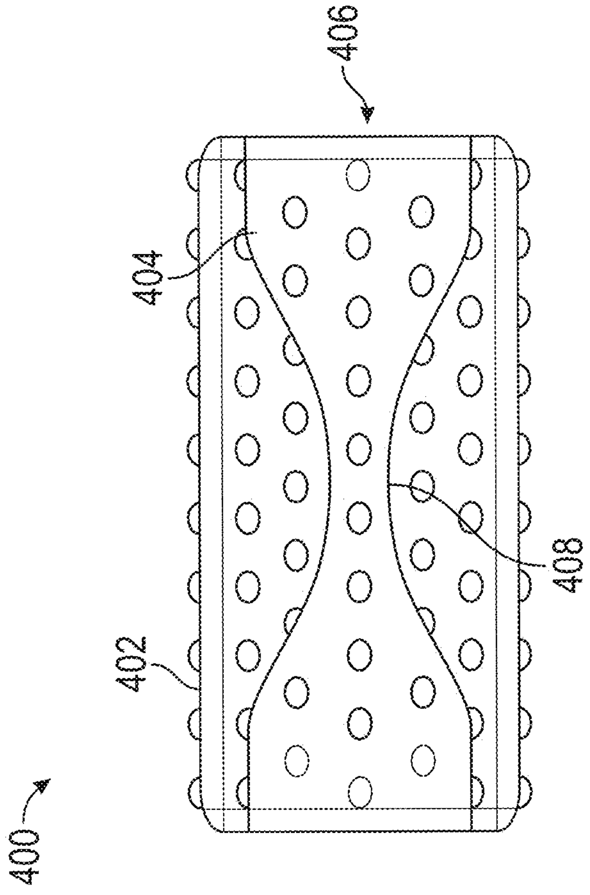

FIGS. 4A and 4B illustrate an example pulmonary implant device 400 with a narrowed lumen to control airflow, in accordance with certain embodiments of the present disclosure. In FIG. 4A, a cylindrical, rod-shaped device 400 with a narrowed inner lumen is shown, and in FIG. 4B, device 400 is shown as being placed in an airway of a targeted lung region of a patient.

As shown in FIG. 4A, example device 400 includes an outer wall 402 and an inner wall 404. The inner wall 404 defines a lumen 406 from a proximal end to a distal end of the device. A diameter of lumen 406 defined in the interior of the device 400 may be slightly smaller than the diameter of device 400 as a whole. However, the diameter of lumen 406 may include a transition portion in which the diameter becomes progressively narrower as it proceeds inward towards a center portion of a length of lumen 406. At its narrowest point 408, lumen 406 creates an obstruction that impairs the flow of air through lumen 406. In certain other embodiments, the cross-sectional diameter of a device's lumen, at all points along the length of the device, may be fixed and may not change over time.

As shown in FIG. 4B, example device 400 may be positioned in a pulmonary region of a patient. In certain embodiments, outer wall 402 of example device 400 is contoured to conform to the pulmonary region of a specific patient. In other words, example device 400 may be patient-specific, and designed according to the respiratory system of the patient. In certain embodiments, outer wall 402 of example device 400 is shaped to fit within an airway within a lung of a respiratory system. In other words, example device 400 may be designed to fit one or more airways of multiple patients.

The minimal cross-sectional diameter of the lumen may be determined based on an analysis of the lung performed prior to implantation of the device in the lung (e.g., referred to as a pre-procedural analysis). In particular, the pre-procedural analysis may return a cross-sectional diameter of the lumen that may be needed to create a desired level of PEEP in airways distal to the airway selected for placement of the device (e.g., to prevent those distal airways from collapsing while inhaling). In certain embodiments, the pre-procedural analysis may take into account the patient's airway where the device is to be implanted and, in some cases, additionally take the progression of a patient's disease into account. For example, the pre-procedural analysis may determine a minimal cross-sectional diameter of a lumen for a patient with a more severe disease diagnosis is greater than a minimal cross-sectional diameter of a lumen for a patient with a mild diagnosis.

In certain other embodiments, the volume defined by the lumen may change over time. For example, the volume may change over time to create a desired level of PEEP in an airway distal to where the device is deployed to prevent those airways from collapsing while exhaling. In some cases, the volume may change to take into account the progression of a disease (e.g., COPD, emphysema, etc.) of a patient. In some cases, the volume may change to prevent a large and/or sudden increase in airflow to neighboring lung regions, which may lead to pneumothorax. Changing the volume of the lumen may include changing the cross-sectional diameter of a device's lumen, at one or more predetermined points along the length of the device, over time, even after the device has been implanted. For example, the cross-sectional area of the lumen may become larger at different point(s) in time, and/or the cross-sectional area of the lumen may become smaller at different point(s) in time.

Further, in certain embodiments, the cross-sectional diameter of the lumen may decrease over time to achieve a higher resistance to airflow. The decreasing of the cross-sectional diameter may help to stabilize and result in a patent lumen (opening).

Figure 5:
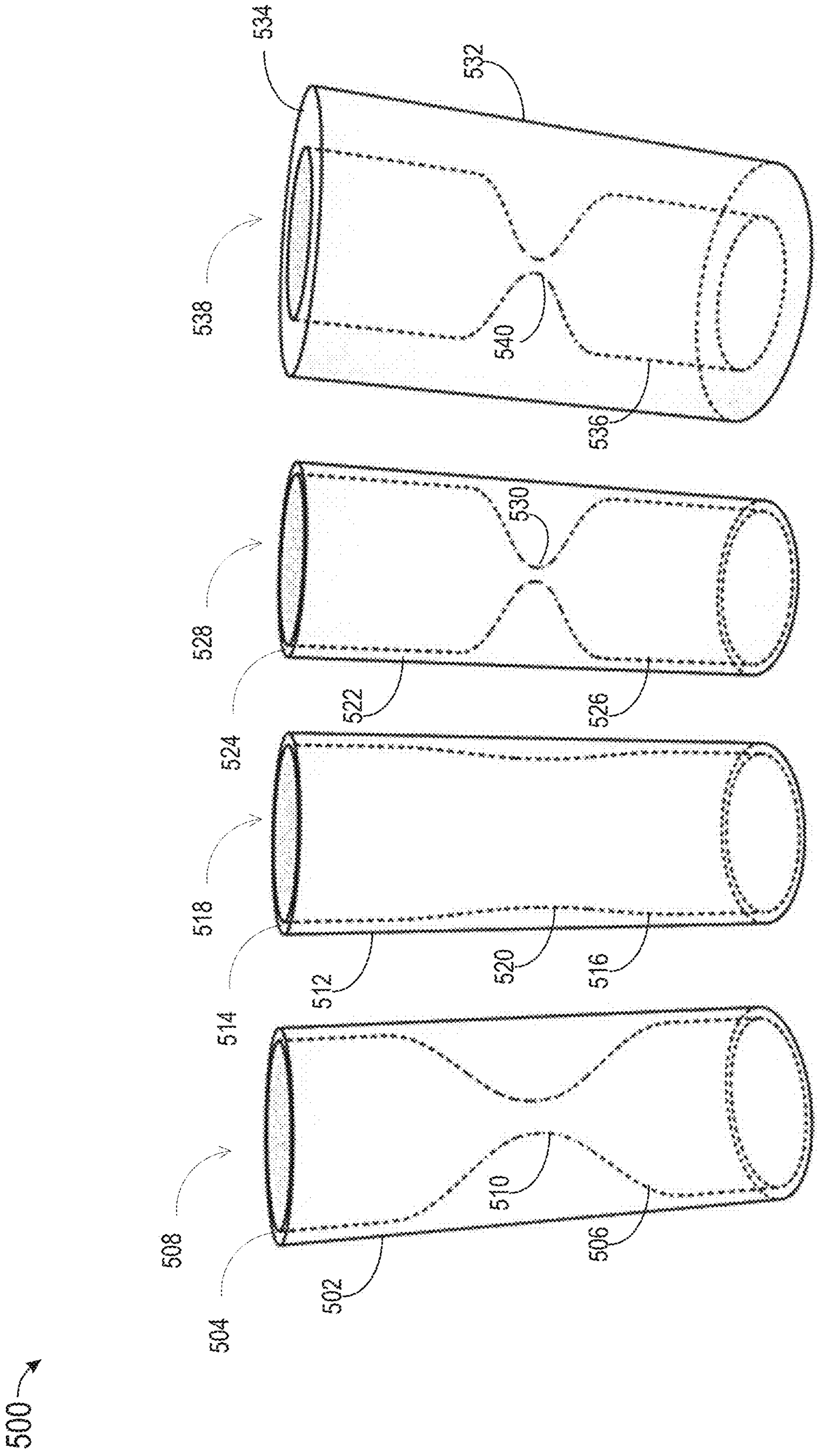
FIG. 5 illustrates example narrowing configurations of different pulmonary implant devices, in accordance with certain embodiments of the present disclosure.

FIG. 5 illustrates example narrowing configurations of different pulmonary implant devices 500, in accordance with certain embodiments of the present disclosure. In particular, FIG. 5 illustrates four different examples of pulmonary implant devices (e.g., devices 502, 512, 522, and 532) with varying lumen volumes to control airflow through an airway. As mentioned, a cross-sectional diameter of the lumen may change along a length of the device to narrow an airway passage of the device, while still allowing for airflow to pass through the device. The four example devices 502, 512, 522, and 532 may be stents and/or stent-like devices that are generally cylindrical in shape. Example devices 502, 512, 522, and/or 532 may include a smooth outer surface. Example devices 502, 512, 522, and 532 are discussed below beginning with the left most device in FIG. 5 (e.g., first example device 502), and proceeding right.

First example device 502 (simply "device 502") illustrated in FIG. 5, may be hollowed such that an outer wall 504 and inner wall 506 are formed. Inner wall 506 may define a lumen 508 (e.g., a hollow channel of device 502). A diameter of inner wall 506 may be slightly smaller than a diameter of device 502 as a whole. However, the diameter of inner wall 506 may become progressively narrower as it proceeds inward towards the center portion of the length of device 502. Diameter 510 represents the narrowest point of the diameter of inner wall 506.

Similar to device 502, second example device 512 (simply "device 512") may be hollowed such that an outer wall 514 and inner wall 516 are formed, where inner wall 516 defines a lumen 518. However, lumen 518 of device 512 may only be slightly narrowed to narrow the airway passage of device 512. In this example, inner wall 516 of lumen 518 does not narrow sharply, but instead narrows only slightly toward an inner diameter 520, which is only slightly smaller than the diameter of outer wall 514. For device 512, airflow may not be altered as significantly as it is in device 502.

Similar to device 502 and device 512, third example device 522 (simply "device 522") may be hollowed such that an outer wall 524 and inner wall 526 are formed, where inner wall 526 defines a lumen 528. As shown in FIG. 5, the lumen 528 extends through device 522 and narrows at location 530 (e.g., inner wall 526 narrows at location 530) such that device 522 is almost completely blocked. Accordingly, for device 522, only a very small amount of air may pass through, and airflow through device 522 may be significantly reduced.

Similar to device 502, device 512, and device 522, fourth example device 532 (simply "device 532") may be hollowed such that an outer wall 534 and inner wall 536 are formed, where inner wall 536 defines a lumen 538. However, a thickness of device 532 between outer wall 534 and inner wall 536 may be greater than devices 502, 512, and 522. This additional thickness may provide additional strength to device 532. Thus, device 532 may be useful for placement in airway passages susceptible to severe constriction and/or other movements that impose severe compressive forces on the outside of device 532. Further, for device 532, inner wall 536 may not extend close to the outer diameter of device 532. As a result, the wall thickness both at the ends of device 532 and toward the center are significantly larger than in devices 502, 512, and 522. However, similar to devices 502 and 522, lumen 538 of device 532 turns sharply inward in the middle portion 540 of device 532 to form an air-passage obstruction. The air-passage obstruction may sharply curtail the amount of air passing through the airway passage.

Differences in airflow for each of devices 502, 512, 522, and 532, and more specifically, differences in resistance to outflowing air, may result in different levels of PEEP. As such, a device positioned in a pulmonary region of a patient may have an inner wall that transitions between each of the different narrowing configurations illustrated in FIG. 5, and/or other narrowing configurations not illustrated in FIG. 5, to change a level of PEEP produced in airways distal to the device. In particular, while FIG. 5 illustrates only four example narrowing configurations, other example narrowing configurations may be considered for initial device design and/or narrowing of the inner wall over time (e.g., after a device has been positioned within a pulmonary region of a patient).

In certain embodiments, at one or more points along the length of a device, the decreasing cross-sectional diameter of the lumen may result in complete occlusion of the lumen, thereby preventing air and/or any other fluid from passing in either direction. Blocking the airway in this way may result in a deflated lung region distal to the device, similar to the desired outcome with EBV devices. However, different from EBV devices, the gradual closure of the inner lumen over time may help to decrease the risk for pneumothorax due to a sudden high increase in airflow to neighboring lung regions while inhaling.

A device may be customized using known systems. One example of a system used in embodiments described herein to customize devices is Materialise Mimics® (e.g., image processing software) made commercially available by Materialise NV of Leuven, Belgium. A device may also be created using one or more techniques of additive manufacturing such as selective laser sintering (SLS), fused deposition modeling (FDM), etc. Further, devices may be made of biocompatible materials such as silicone, nitinol, polylactic acid (PLLA) (bioresorbable), etc. To decrease the risk of foreign body reactions, infection, and/or inflammation, one or more surfaces of the device may be coated with a specific drug substance and/or may be drug eluting.

Figure 6A:
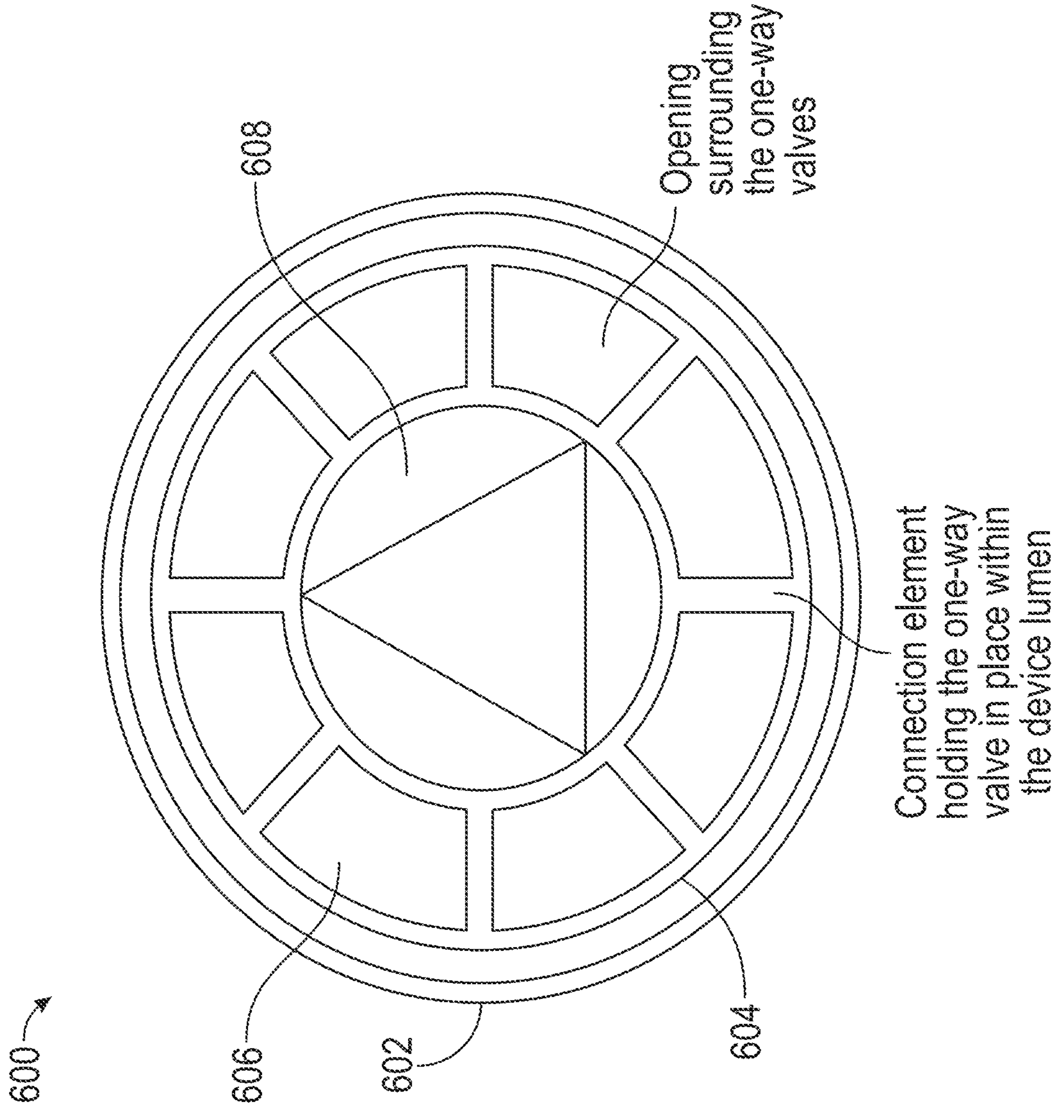
FIG. 6A illustrates an example one-way valve positioned in a lumen of a pulmonary implant device, in accordance with certain embodiments of the present disclosure.

In certain embodiments, a one-way valve (e.g., a device that allows the flow of fluid(s) to move only in one direction) may be positioned within the lumen of a device described herein. FIG. 6A illustrates an example one-way valve positioned in a lumen of a pulmonary implant device 600, in accordance with certain embodiments of the present disclosure.

As illustrated in FIG. 6A, device 600 is hollowed such that an outer wall 602 and inner wall 604 are formed, where inner wall 604 defines a lumen 606. Further, a one-way valve 608 is positioned within lumen 606.

One-way valve 608 may be attached to inner wall 604 of lumen 606 by connection elements. For example, one-way valve 608 may be connected to inner wall 604 by beams. In another example, one-way valve 608 may be fixed in a mesh-like structure, or membrane, that contains openings to allow air to flow through, at one or more points within lumen 606.

In certain embodiments, one-way valve 608 is configured to permit airflow in a first direction through one-way valve 608 and prevent airflow in a second direction through one-way valve 608. For example, one-way valve 608 may allow for fluid to flow from a distal end of lumen 606 to a proximal end of lumen 606 (i.e. towards a patient's mouth, such as during expiration).

In a first configuration of device 600, there may be a gap between at least a portion of one-way valve 608 and inner wall 604. The gap may be configured to permit airflow in both the first direction and the second direction through the lumen 606 from the proximal end to the distal end of device 600. For example, in certain embodiments, by incorporating one-way valve 608 within lumen 606, air may be allowed to flow through one-way valve 608 in one direction, and through the openings of the mesh in the other direction.

Alternatively, in a second configuration of device 600, no gap may exist between one-way valve 608 and the inner wall 604. For example, in certain other embodiments, the mesh-like structure or membrane may be blocked or closed to make device 600 into a unidirectional device where air flows only through one-way valve 608. The mesh-like structure may be used for rigidity to hold one-way valve 608 in place in lumen 606 of device 600 when implanted in an airway.

Figure 6B:
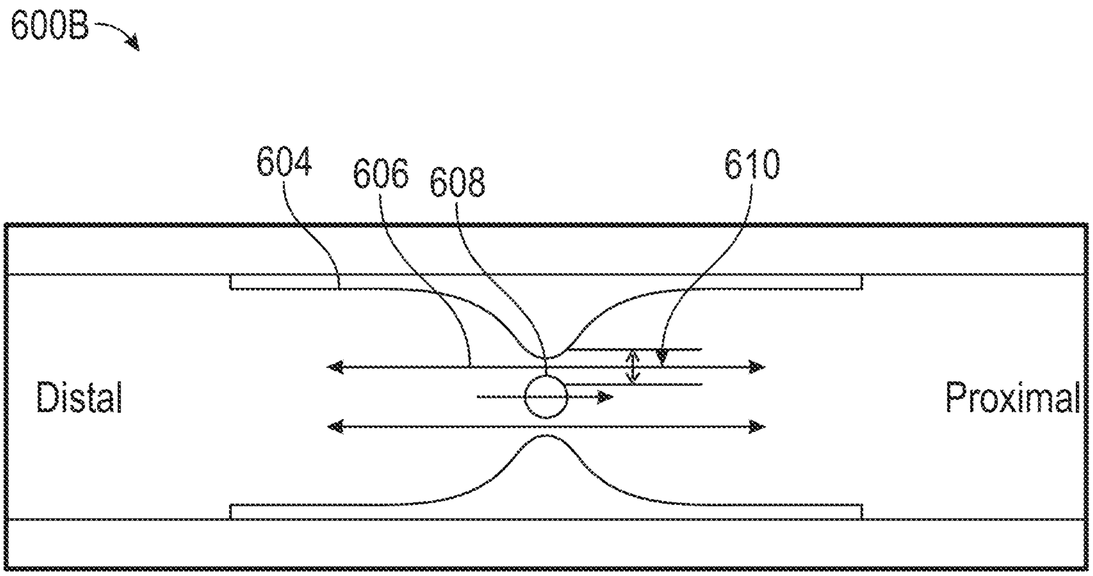
FIGS. 6B and 6C illustrate example narrowing of an inner wall of a pulmonary implant device around a one-way valve positioned within the device, in accordance with certain embodiments of the present disclosure.
Figure 6C:
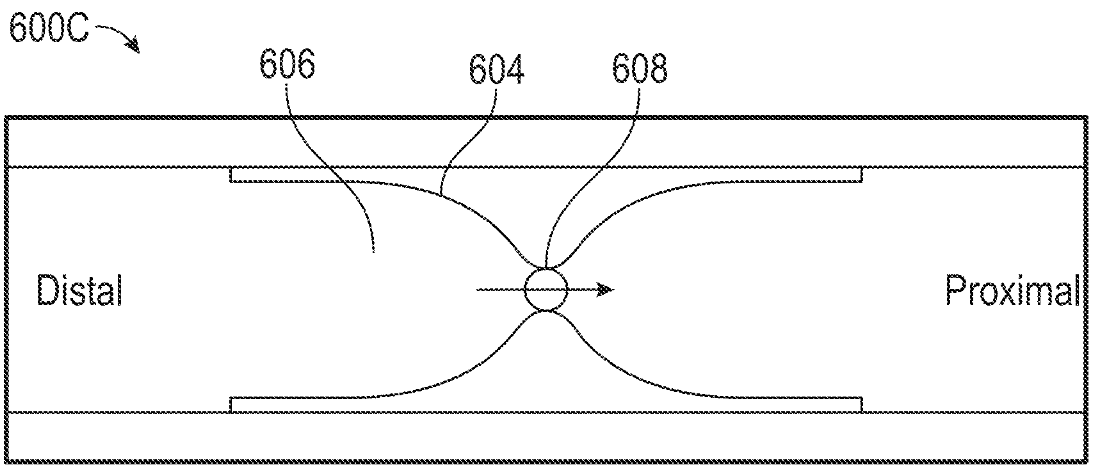

In certain embodiments, device 600 is configured to transition between the first configuration and the second configuration. In other words, inner wall 604 of device 600 may be narrowed to transition device 600 from the first configuration to the second configuration. FIGS. 6B and 6C illustrate example narrowing of inner wall 604 of device 600 around one-way valve 608 positioned within device 600, in accordance with certain embodiments of the present disclosure.

As shown in FIG. 6B, in a first configuration 600B, a gap 610 exists between at least a portion of one-way valve 608 and inner wall 604. Gap 610 allows for bidirectional airflow in device 600. In certain embodiments, device 600 may transition from first configuration 600B illustrated in FIG. 6B to second configuration 600C illustrated in FIG. 6C. To transition between first configuration 600B and second configuration 600C, a volume of lumen 606 may change, and more specifically, a cross-sectional diameter of lumen 606 (e.g., inner wall 604) may change. As shown in FIG. 6C, in second configuration 600C, inner wall 604 is progressively narrowed near a center of device 600 (e.g., and near one-way valve 608). Inner wall 604 may be narrowed such that gap 610 no longer exists between one-way valve 608 and inner wall 604. As such, air may flow only through one-way valve 608 (e.g., airflow may be unidirectional).

In certain embodiments, the inner wall and/or the outer wall of the device described herein includes a material configured to transition the device between the first configuration and the second configuration based on temperature. In particular, deformation of the inner wall of the device (e.g., to cause a change in volume of the lumen) may rely on temperature applied to the entire device or to one or more portions of the device.

The device may be made of one or more materials that are temperature-sensitive and/or may be coated with one or more temperature-sensitive substance(s) to enable such temperature-induced deformation. Thus, the diameter of the inner wall may be altered at one or more determined points along the device length based on the temperature applied to the one or more materials.

In some cases, the alteration and/or change in the cross-sectional diameter of the inner wall may be induced due to a change in the temperature of the surrounding tissue. For example, the temperature-sensitive material may respond to temperature ranges which include body temperature. Accordingly, the change in shape of the inner wall may be triggered immediately after implantation of the device. As another example, the temperature-sensitive material may respond to much warmer or cooler temperatures than body temperature and/or inhaled air. For example, the change in shape of the inner wall may be triggered by applying an external heat source during a bronchoscopy intervention.

In some cases, the alteration and/or change in the cross-sectional diameter of the inner wall may be induced by an external source. In particular, the temperature-sensitive material may respond to much warmer or cooler temperatures than body temperature and/or inhaled air. Thus, the change in shape of the inner wall may be triggered by applying an external heat or cooling source during, for example, a bronchoscopy intervention. An external heat source may be an instrument with a heat source in the tip that is applied to the device through flexible bronchoscopy. The temperature change may be hotter or colder than the actual temperature of and/or that surrounding a device.

In certain embodiments, the inner wall and/or the outer wall of the device described herein includes a material configured to transition the device between the first configuration and the second configuration based on a magnetic field. In particular, deformation of the inner wall of the device (e.g., to cause a change in volume of the lumen) may rely on a magnetic field applied to the entire device and/or to one or more parts of the device. An external magnetic source may be an instrument with a magnetic source (such as magnet) in the tip that is applied to the device through a flexible bronchoscopy.

In certain embodiments, the device may include one or more chambers formed between an outer wall and an inner wall of the device. The chambers may be filled with temperature-sensitive material and/or material responsive to changes in magnetic field. The chambers may have essentially separate pathways to allow for individual filling of each of the chambers with the temperature-sensitive material and/or the material responsive to changes in magnetic field.

When the one or more chambers are at least partially filled with such material, the chambers may be configured to narrow a cross-sectional diameter of the device. In certain embodiments, when the one or more chambers are at least partially filled, the chambers may be configured to transition the device to the second configuration (e.g., shown in FIG. 6C) without the gap between the one-way valve and the inner wall and the device.

Figure 7A:
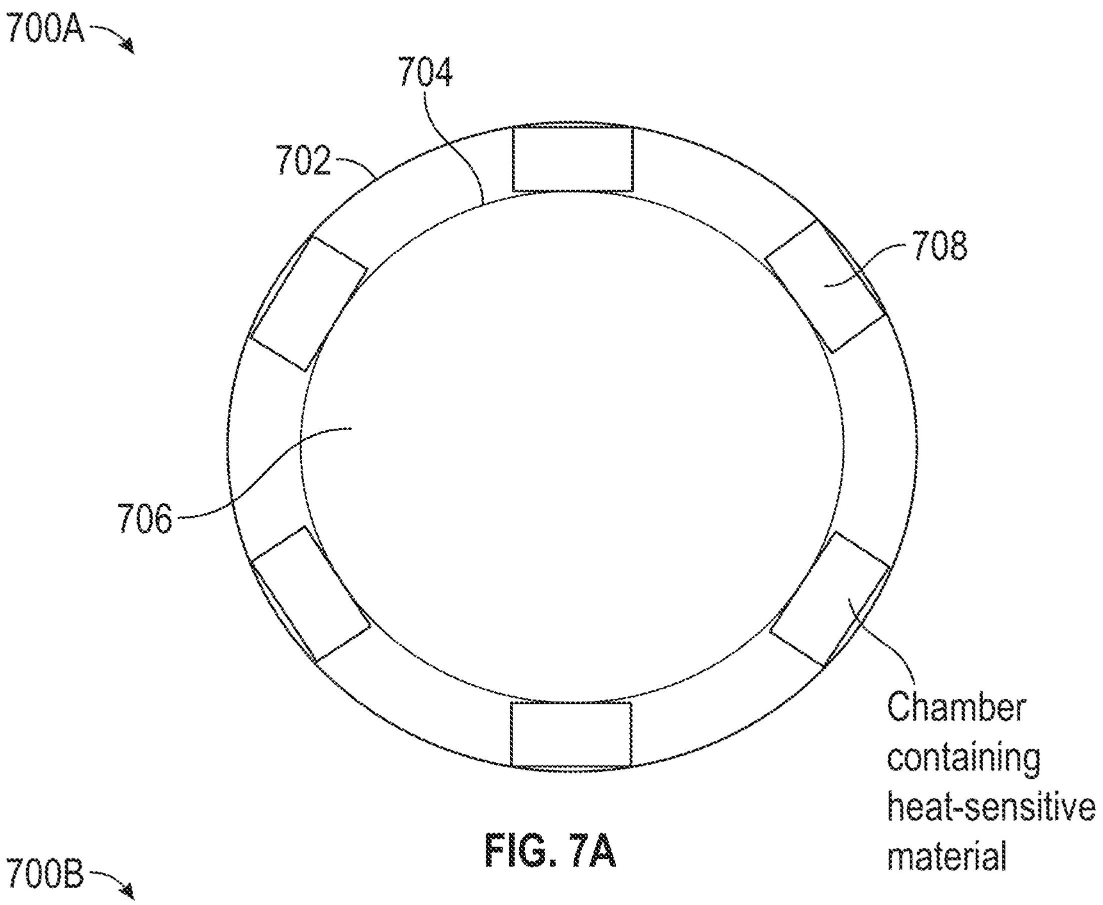
FIGS. 7A and 7B illustrate an example change to the volume of a device's lumen based on a change in an amount of material in at least one chamber of the device, in accordance with certain embodiments of the present disclosure.
Figure 7B:
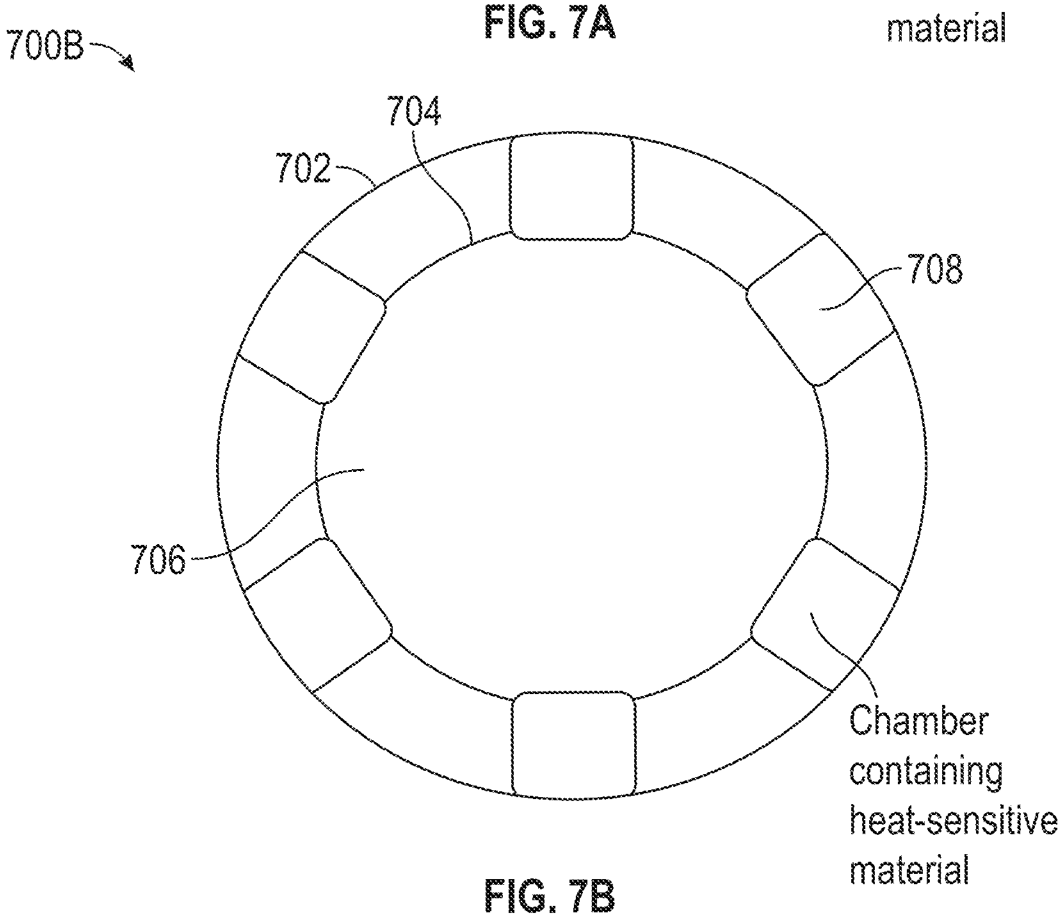

FIGS. 7A and 7B illustrate an example change to the volume of a device's lumen based on a change in amount of material in at least one chamber of a device, in accordance with certain embodiments of the present disclosure. The material may be material configured to change shape or volume based on temperature and/or material configured to change based on magnetic field. As illustrated, in FIGS. 7A and 7B, the device is hollowed such that an outer wall 702 and inner wall 704 are formed, where inner wall 704 defines a lumen 706. Although not illustrated, in some cases, a one-way valve may be positioned within lumen 706 (e.g., as illustrated in FIGS. 6A, 6B, and 6C).

One or more chambers 708 may be formed between outer wall 702 and inner wall 704 of the device. For example, as illustrated, six chambers 708 are formed in the device. Chambers 708 may be hollow spaces between inner wall 704 and outer wall 702 of the device; however, chambers 708 may be filled/injected (during the process of manufacturing or after) with temperature-sensitive material and/or material that is responsive to changes in magnetic field to cause a change in volume of lumen 706. Chambers 708 may extend the entire length of the device or less than all of the length of the device.

In some cases, a change in volume or shape of material added to chambers 708 may result in narrowing of inner wall 704, and thus a decrease in the volume of lumen 706. For example, as illustrated in FIG. 7A, chambers 708 for the device shown, at a first time 700A, may include material that occupies a first volume, while at a second time 700B shown in FIG. 7B, the material may occupy a second volume. The second volume may be greater than the first volume (e.g., shown by larger chambers 708 in FIG. 7B than chambers 708 in FIG. 7A). Thus, when a change in temperature and/or a change in magnetic field is applied to the material, the device shown at second time 700B may have a smaller lumen volume than the device shown at first time 700A.

Chambers 708 of different devices may have different geometries, sizes, capacities, and/or the like. In certain embodiments, each chamber 708 may be filled with a same amount of material. In certain other embodiments, one or more chambers 708 may be filled with different amounts of material. As such, each chamber 708 may be coupled to a separate fluid path such that each chamber 708 can be separately filled with fluid via its own separate fluid path (or different chambers 708 may be coupled to different fluid paths, where at least two fluid paths exist), as opposed to all chambers 708 being coupled to a shared fluid path such that all chambers 708 would be filled with fluid via a shared fluid path. For example, a first chamber 708 may be coupled to a first fluid path through the outer wall 702, and a second chamber 708 may be coupled to a second fluid path through the outer wall 702. The first fluid path may be separate from the second fluid path.

In certain embodiments, deformation of the inner wall of the device (e.g., to cause a change in volume of the lumen) may rely on pressure applied to the entire device or to one or more parts of the device. In particular, the device may be made of one or more materials that are pressure-sensitive and/or may be coated with one or more pressure-sensitive substances to enable such pressure-induced deformation.

In certain embodiments, changing the volume of the lumen may include applying an external pressure to the device. The external pressure may be applied to the entire device or to one or more parts of the device. As such, the cross-sectional diameter of the lumen (e.g., the inner wall) may be altered at one or more points along the device length. The external pressure may be applied prior to placing the device in a targeted lung region, and more specifically, in a selected airway passage. For example, the pressure may be induced by an external source at the time of packaging or preparing of the device prior to implantation. After removing the external pressure on the device and implanting the device in a preselected airway, the cross-sectional narrowing at one or more multiple points along the device length may be altered.

In certain embodiments, the external pressure may be applied to the inner wall of the lumen prior to implanting the device to keep the lumen at a particular diameter. However, when the device is implanted, the external pressure may be removed thereby allowing the inner wall of the lumen to deform to its steady-state. This deformation may include a narrowing of the inner wall of the lumen over time.

Figure 8A:
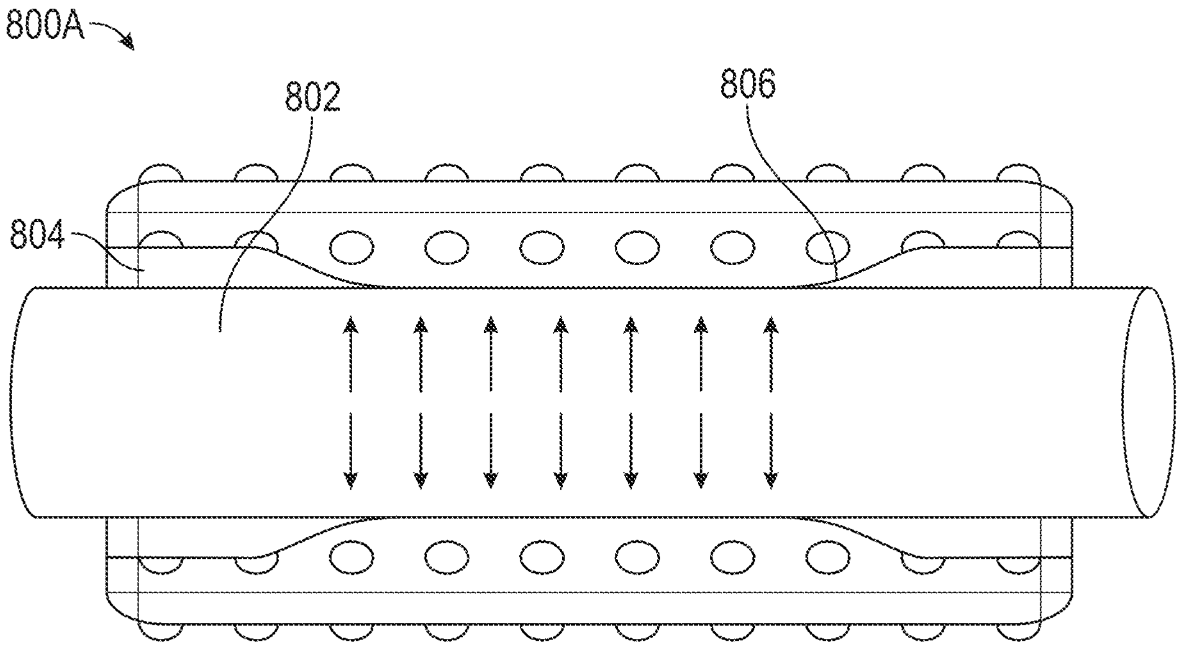
FIGS. 8A and 8B illustrate example narrowing of an inner wall of a pulmonary implant device subsequent to the removal of external pressure applied to the device, in accordance with certain embodiments of the present disclosure.
Figure 8B:
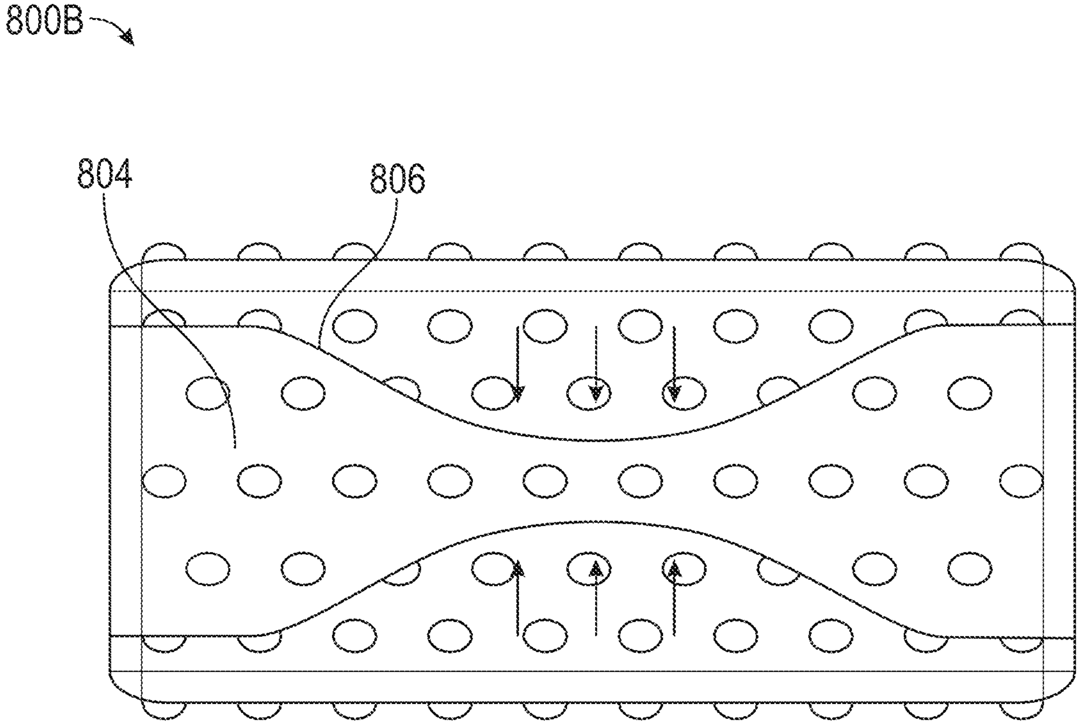

FIGS. 8A and 8B illustrate example narrowing of an inner wall of a pulmonary implant device subsequent to the removal of external pressure applied to the device, in accordance with certain embodiments of the present disclosure. In particular, FIG. 8A illustrates a device at a first time 800A prior to implantation of the device, having an external device 802 positioned in a lumen 804 of the device to exert pressure on an inner wall 806 of the device. On the other hand, FIG. 8B illustrates the device at a second time 800B after implantation of the device, where the external device 802 has been removed from lumen 804 of the device.

In some cases, external device 802 may be a "placeholder" strut positioned in lumen 804 of the device prior to implantation. For example, when packaging the device, the "placeholder" strut may be positioned in the lumen to exert pressure on inner wall 806 and keep the lumen at a certain diameter. Immediately prior to implanting (or some other time prior to implanting), the "placeholder" strut may be removed, and then the device may be implanted. Thus, by removing the "placeholder" strut prior to implantation, pressure exerted on inner wall 806 of lumen 804 may be released. By releasing the pressure, inner wall 806 may deform thereby causing lumen 804 to narrow over time back to its steady-state. Narrowing of the lumen subsequent to removal of the "placeholder" strut is illustrated in FIG. 8B.

In certain embodiments, the external pressure may be applied to the inner wall of the lumen subsequent to implanting the device. For example, external pressure may be applied via balloon dilation. More specifically, an external, deflated balloon may be introduced into the lumen of a device. The balloon may then be inflated, thereby inducing pressure on the inner wall of the lumen to deform and cause an increase in the cross-sectional diameter of the inner wall of the lumen at one or more points along the length of the device.

Figure 9:
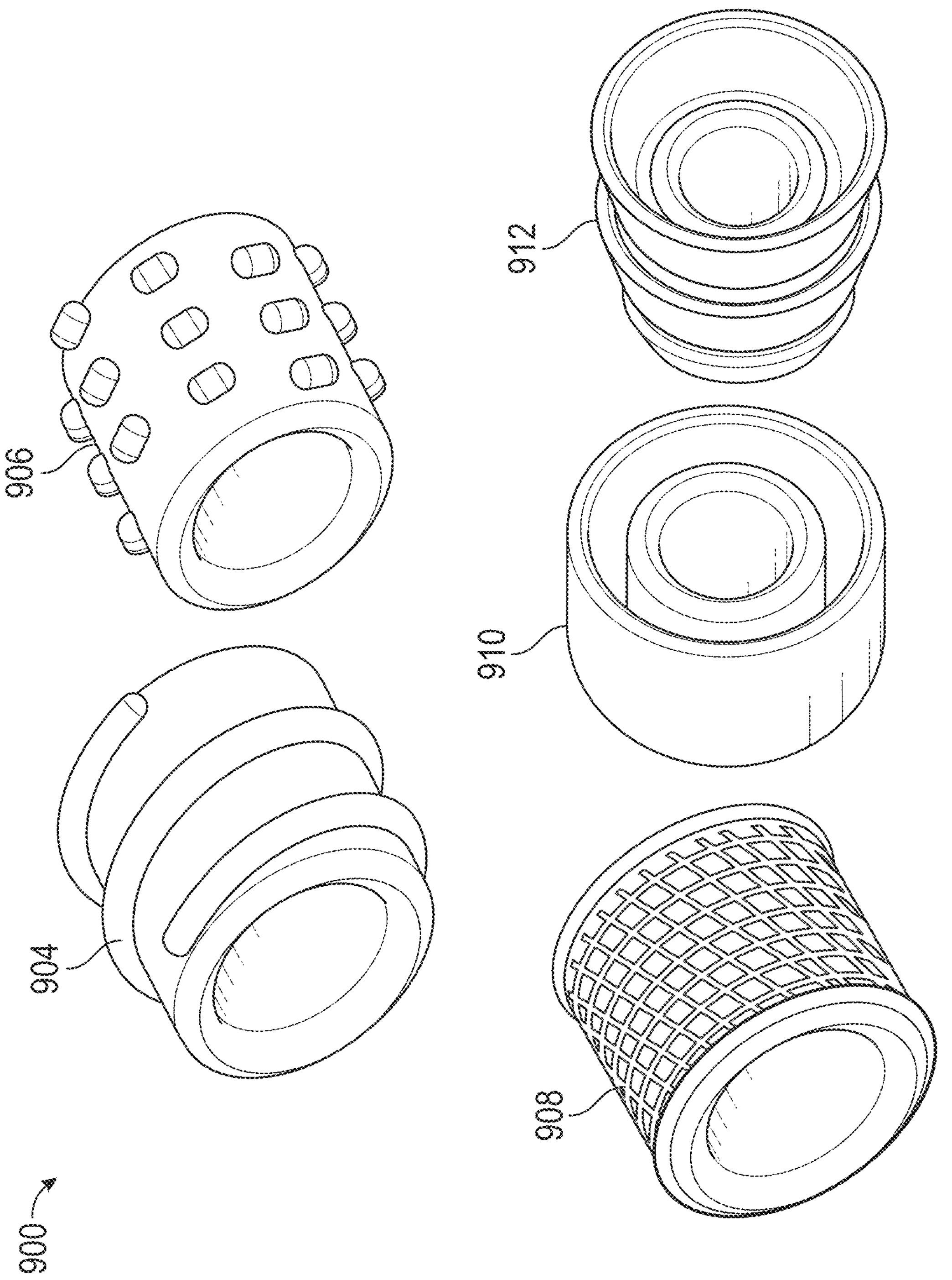
FIG. 9 illustrates example outer surface components and patterns of different pulmonary implant devices used to prevent migration of these devices, in accordance with certain embodiments of the present disclosure.

In certain embodiments, an outer surface of the device described herein may be designed to prevent migration of the device after placement and/or implantation. Accordingly, to prevent such migration, the device may include elements and/or features such as raised portion(s), protrusion(s), and/or embossed portion(s) on the outer surface of the outer wall of the device. Such elements and/or features may help to provide resistance to movement and/or migration of the device by roughening the outer surface of the outer wall without causing damage to the surrounding tissue. In some cases, raised portion(s) and/or protrusion(s) include stud(s), raised or embossed line(s) of certain thickness and/or pattern, etc. The line(s) may be straight, curved, crisscross, zigzag, or include a combination thereof. Other additions to roughen and/or add resistance to the outer wall surface may also be considered and used herein. In certain embodiments, there may be a second shell circumventing the outer surface of the outer wall, with multiple compressible elements, or a mesh-like structure, connecting the shell with the outer surface. The connection elements may be beams that are straight and/or curved. To help prevent the device from migrating, the cross-sectional diameter of the shell may be determined based on the diameter of the airway at inhalation when it is largest. Accordingly, when a patient exhales, the airway may constrict, the connection elements may be compressed such that the shell moves closer to the outer surface, and due to the radial pressure, the device may not migrate. FIG. 9 illustrates example outer surface components and patterns of different pulmonary implant devices 904-912 to prevent migration of these devices, in accordance with certain embodiments of the present disclosure.

In certain embodiments, an inner wall of the device described herein may be at least partially coated with a coating material comprising (super-) hydrophobic characteristics and/or (super-) hydrophilic characteristics. In particular, the inner wall may be treated to possess such characteristics, for example, by oxidation further treated with steric acid, treatment with chemical etching compounds copper chloride ($CuCl_2$) and/or hydrogen chloride (HCl), or by treatment with biocompatible (super-) hydrophobic and/or (super-) hydrophilic substances such as platinum modified fibrous carbon mesh, Parylene, Aculon® or polymers. Alternatively, one or more (bio)molecules such as polyethylene glycol (PEG) may also be used. A person skilled in the art will appreciate and understand that other suitable substances that generate the same effect may be used, and that the above-mentioned list of substances is not limiting. Nanocoating may be used to treat the surface of the inner wall by coating it with (bio)molecules. A person skilled in the art will be familiar with the technique of nanocoating and be able to select the appropriate technique for the device.

In certain embodiments, the surface of the inner wall may be coated with the chosen coating material comprising (super-) hydrophobic characteristics and/or (super-) hydrophilic characteristics to prevent mucus from getting trapped in a lumen of the device, and in some cases, blocking the lumen/airways. For example, the material may stimulate mucus and/or other secretions to flow in one specific direction (i.e., from the distal to proximal end (in the outward direction)), thereby preventing the mucus and/or other secretions from flowing in the other direction (i.e., from the proximal to distal end (inward towards the interior of the targeted lung region)). This guided secretion of the mucus towards the proximal end prevents mucus from blocking the lumen/airway by stimulating mucus clearance, thereby reducing chances of regional hyperinflation due to mucus plugging. As an illustrative example, in certain embodiments, the surface of the inner wall may be coated with a chosen (bio)molecule such that the hydrophobicity or hydrophilicity gradually decreases along the device length distally to proximally, thereby stimulating mucus and/or other secretions to flow out of the device in the direction of the mouth. The coatings may be formed using a coupling agent.

In certain embodiments, the surface of the inner wall may be treated in specific patterns at the time of manufacturing to assist in adherence of an increasing concentration of the substances from one end of the device to the other, to thereby enable difference in intensity of the hydrophobicity and/or hydrophilicity either in a decreasing or increasing magnitude from one end of the device to another. As such, this may to enable unidirectional flow of secretions. For example, this may be achieved at the time of designing the device and printing the device using additive manufacturing (3D printing) such as selective lasering. Other additive manufacturing techniques known in the art may also be used. Additionally, the device may be treated to add a layer of (bio)molecule via nanocoating.

Figure 10:
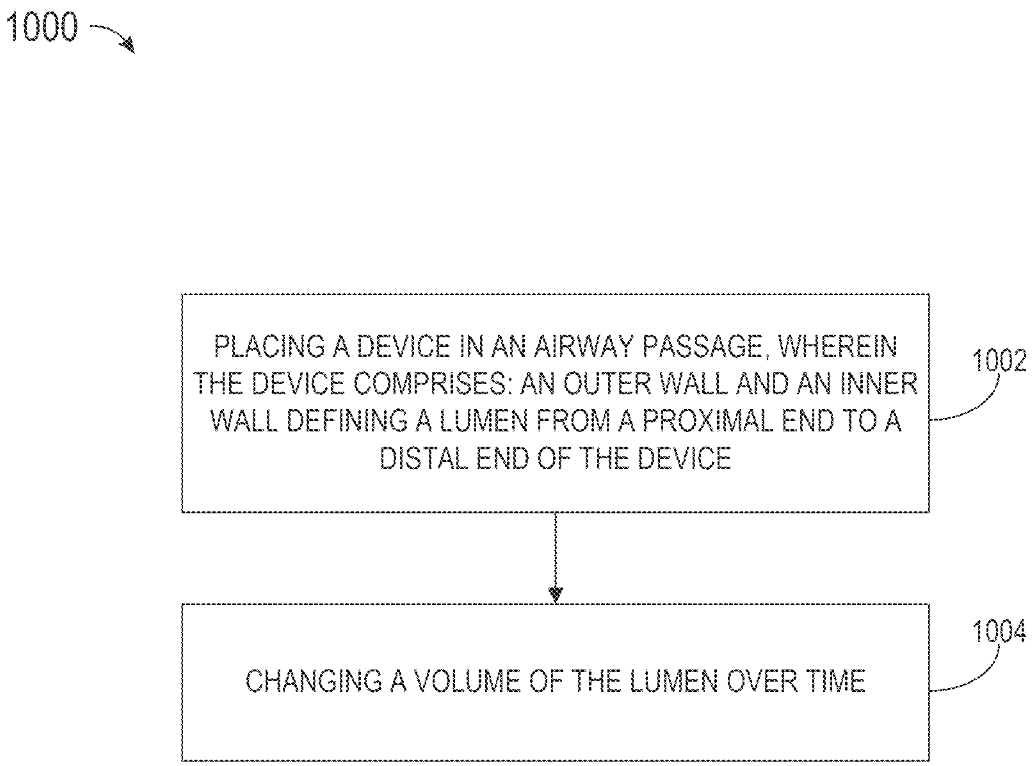
FIG. 10 is a flow diagram illustrating example operations for controlling airflow in a lung of a respiratory system of a patient, in accordance with certain embodiments of the present disclosure.

Example Method for Controlling Airflow in a Lung of a Respiratory System of a Patient FIG. 10 is a flow diagram illustrating example operations 1000 for controlling airflow in a lung of a respiratory system of a patient, in accordance with certain embodiments of the present disclosure.

As illustrated, operations 1000 begin, at block 1002, with placing a device (e.g., a pulmonary implant device) in an airway passage. The airway passage may be in a lung of a respiratory system of a patient. The device may include an outer wall and an inner wall defining a lumen from a proximal end to a distal end of the device.

At block 1004, operations 1000 proceed with changing a volume of the lumen over time.

As described in detail above, the lumen of the device may be narrowed gradually over time after placement of the device to change a volume of the device's lumen. For example, as respiratory conditions/diseases, such as COPD (type emphysema), progress in a patient, higher levels of PEEP may be required to prevent airways, distal to an airway where the device is placed, from collapsing. Accordingly, the inner wall of the lumen may be narrowed gradually to increase resistance to outflowing air, and thus create PEEP. The created PEEP may help to prevent airways and/or alveoli distal to the device from collapsing, thereby facilitating deflation of targeted lung region(s) and/or lobe(s) while further improving regional ventilation/perfusion. Further, as the device lumen gradually narrows over a certain period of time, the device may not need to be replaced with another device with a narrower lumen once the disease has progressed to a stage in which a higher level of PEEP is needed to prevent airway collapse.

Figure 11:
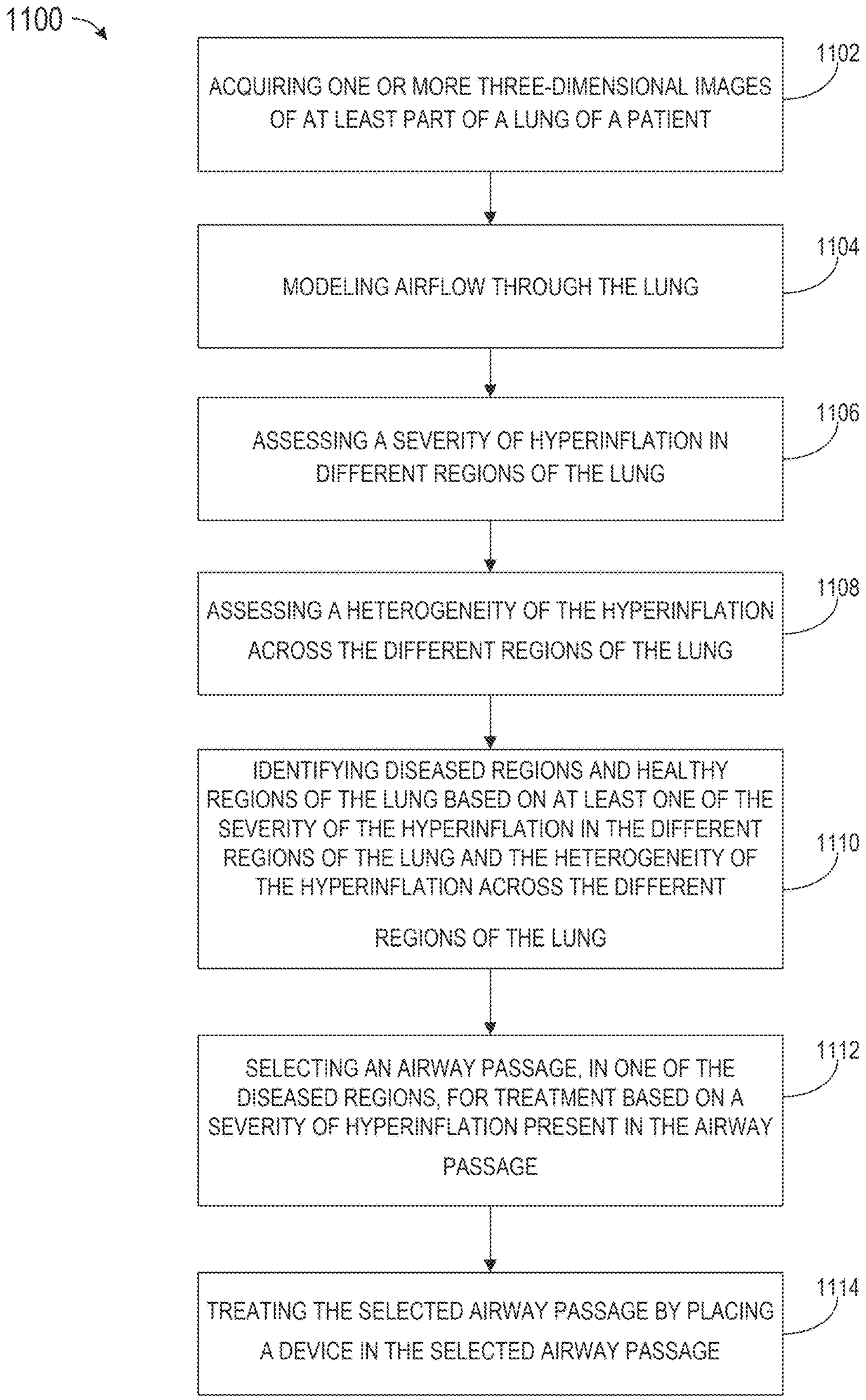
FIG. 11 is a flow diagram illustrating example operations for placing a pulmonary implant device, in accordance with certain embodiments of the present disclosure.

FIG. 11 is a flow diagram illustrating example operations 1100 for placing the device in an airway passage, in accordance with certain embodiments of the present disclosure. In particular, operations 1100 provide more detail for placing the device in the airway passage at block 1002 in FIG. 10.

As illustrated, operations 1100 begin, at block 1102, with acquiring one or more three-dimensional images of at least part of a lung of a patient. For example, medical images of a patient's chest may be obtained and converted into three-dimensional images. The images may include CT scans obtained using standard protocols.

At block 1104, operations 1100 proceed with modeling airflow through the lung. For example, in certain embodiments, a first computer model of airflow through at least part of the lung of the patient may be generated. Generating the first computer model of the airflow through at least the part of the lung may include performing a functional respiratory imaging (FRI) analysis and/or quantitative computed tomography (qCT).

At block 1106, operations 1100 proceed with assessing a severity of hyperinflation in different regions of the lung. Further, at block 1108, operations 1100 proceed with assessing a heterogeneity of the hyperinflation across the different regions of the lung.

At block 1110, operations 1100 proceed with identifying diseased regions and healthy regions of the lung based on at least one of the severity of the hyperinflation in the different regions of the lung and the heterogeneity of the hyperinflation across the different regions of the lung. Diseased regions of the lung that are identified may be hyperinflated regions of the lung, while healthy regions of the lung may be regions of the lung not showing signs of hyperinflation.

Based on the identified diseased and/or healthy regions of the patient, a clinician may decide (or a device configured to make this determination) if this patient is a candidate for treatment (e.g., a candidate for having the device implanted in one or more airway passages of the patient). Where the clinician (or device) determines that the patient is a candidate for treatment, operations 1100 proceed to block 1112.

At block 1112, operations 1100 include selecting an airway passage, in one of the diseased regions, for treatment based on a severity of hyperinflation present in the airway passage.

For example, a targeted lung region for placing the device may be a lung region that shows the highest severity of hyperinflation. In certain embodiments, one or more airway passages in the lung region may be chosen for implantation of one or more devices.

In certain embodiments, an algorithm may be used to determine one or more targeted lung regions for treatment based on hyperinflation severity and/or heterogeneity. For example, the algorithm identifies which regions of the lungs are hyperinflated. If the patient presents with a heterogeneous pattern of hyperinflation across the lungs, the most affected regions may be targeted for treatment. The algorithm may act upon a fixed, pre-defined protocol, or by incorporating in parts, or in whole, a deep learning-based model. Once the one or more targeted lung regions for treatment are identified, the operator and/or an automated algorithm may identify the target device location (e.g., a selected airway passage for placement of the device). The target device locations may be based on targeted lung regions what are most affected by hyperinflation and/or which target device locations have a shape and/or length suitable for fitting the device.

At block 1114, operations 1100 proceed with treating the selected airway passage by placing a device in the selected airway passage.

In certain embodiments, one or more devices may be implanted in neighboring airways that supply a targeted lung region to reduce the risk for pneumothorax following the placement of devices, like stents and/or EBVs. In particular, devices described herein may be designed to be placed in the left or right main stem, lobar, segmental, and/or sub-segmental airway branch(es) (e.g., as depicted and described with respect to FIG. 1) that supply the targeted lung region(s), and/or its surrounding lung region(s).

In certain embodiments, devices described herein are designed based on medical imaging in any preplanning software, modules, and/or systems embedded with such software and/or modules. In certain embodiments, devices described herein are designed based on a 3D model of the patient's anatomy derived from medical imaging.

As such, in certain embodiments, devices described herein may be patient-specific (e.g., designed to fit the patient's anatomy). In certain other embodiments, devices described herein may be selected from a range of shapes and/or sizes that best match a patient's anatomy. For example, a device may be selected from a plurality of devices that do not exceed a length of a target airway branch, and/or that have a diameter that is slightly larger than the (estimated) largest diameter of the airway of a patient while inhaling. In particular, over-sizing the device in diameter may result in a press-fit and/or radial force that reduces the risk for migration of the device.

In certain embodiments, an outer wall of such devices described herein are designed to fit the location of its placement. For example, a device may be designed to match a regional shape of an inner airway wall. A device may be personalized, customized, patient-specific, or patient-matched in nature i.e., designed to match a patient's anatomy or anatomical region for a better fit. Alternatively, a device may be a standard, off-the shelf device that may be modified to match a patient's anatomy and/or anatomical region for a better fit.

In addition to designing the device to fit within the selected airway passage, in certain embodiments, an initial volume of the lumen of the device may be determined prior to placing the device in the airway passage. In particular, determining an initial volume of the lumen may include determining a diameter of the narrowest cross-section of a lumen of the device. For example, a diameter of the narrowest cross-section may be determined such that the device creates a positive pressure that is sufficient to avoid collapse of airways distal to the selected airway passage where the device is to be placed (e.g., when a patient exhales).

Figure 12:
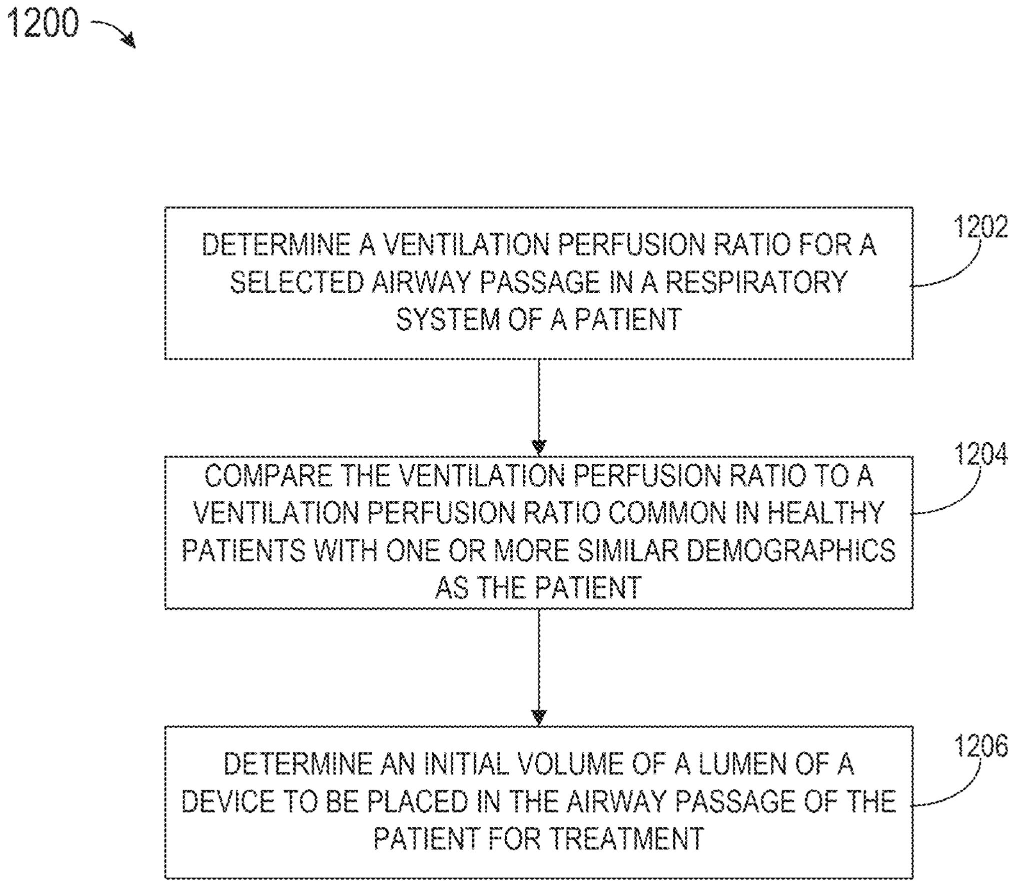
FIG. 12 is a flow diagram illustrating example operations for determining an initial volume of a lumen of a pulmonary implant device, in accordance with certain embodiments of the present disclosure.

FIG. 12 is a flow diagram illustrating example operations 1200 for determining an initial volume of a lumen of a pulmonary implant device, in accordance with certain embodiments of the present disclosure.

As illustrated, operations 1200 begin, at block 1202, with determining a ventilation perfusion ratio for a selected airway passage in a respiratory system of a patient. For example, the selected airway passage may be an airway passage selected at block 1112 in FIG. 11. The relationship between ventilation and perfusion in a lung region is expressed as the ventilation perfusion ratio (V/Q).

In certain embodiments, determining the ventilation perfusion ratio for the airway passage includes (1) determining an inspiratory capacity of the patient, (2) determining a blood vessel volume of the selected airway passage, and (3) dividing the inspiratory capacity by the blood vessel volume of the airway passage. The blood vessel volume of the airway passage is based on a number of blood vessels present in the airway passage, the blood vessels having a cross-sectional area less than a threshold cross-sectional area.

At block 1204, operations 1200 proceed with comparing the ventilation perfusion ratio to a ventilation perfusion ratio common in healthy patients with one or more similar demographics as the patient.

At block 1206, operations 1200 proceed with determining the initial volume of the lumen based on the comparison. An initial diameter along a length of the lumen of the device (e.g., where the diameter is kept constant), or multiple diameters along the length of the lumen of the device, may be determined based on the determined initial volume of the lumen. The device may be designed according to this determination.

Figure 13:
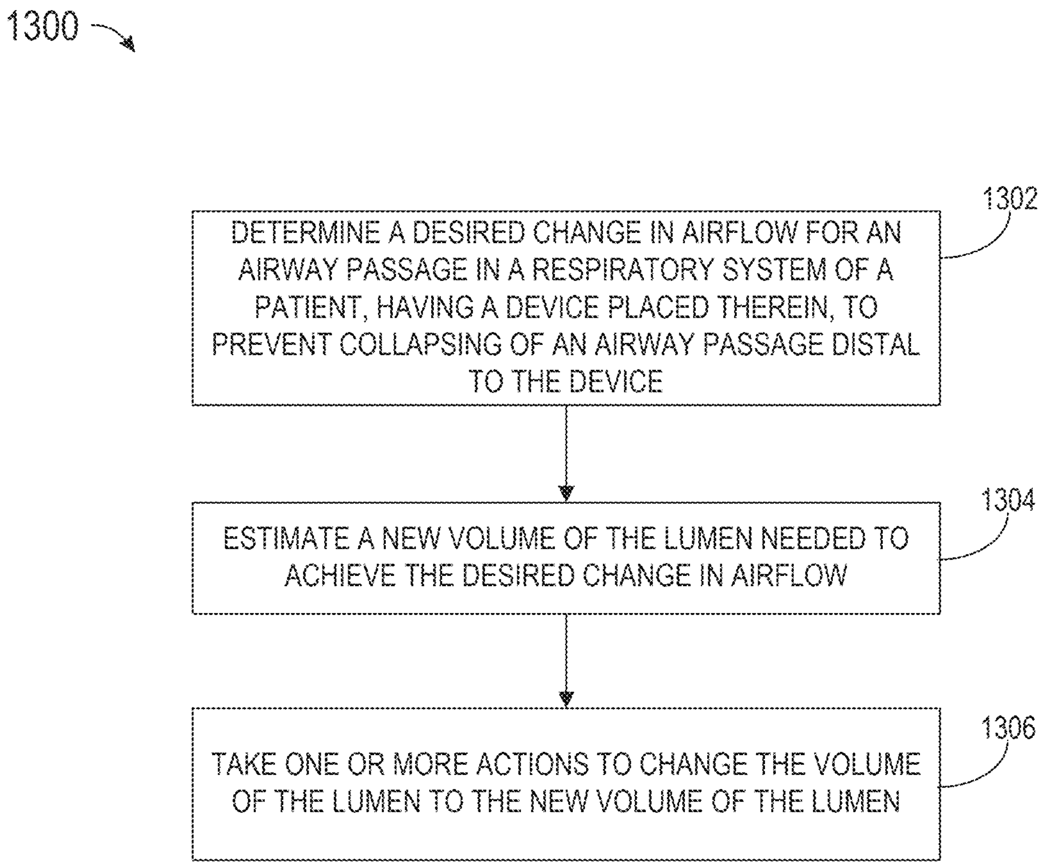
FIG. 13 is a flow diagram illustrating example operations for changing a volume of a lumen of a pulmonary implant device after deployment, in accordance with certain embodiments of the present disclosure.

After design of a device and placement of the device in a selected airway passage for treatment, in certain embodiments, the volume of a lumen of the device may gradually change over time. The volume of the lumen may gradually change over time to prevent collapsing of one or more airway passages distal to the device. FIG. 13 is a flow diagram illustrating example operations for changing a volume of the lumen of the device, in accordance with certain embodiments of the present disclosure.

As illustrated, operations 1300 begin, at block 1302, with determining a desired change in airflow for the selected airway passage, having the device placed therein, to prevent collapsing of an airway passage distal to the device.

At block 1304, operations 1300 proceed with estimating a new volume of the lumen needed to achieve the desired change in airflow.

At block 1306, operations 1300 proceed with taking one or more actions to change the volume of the lumen to the new volume of the lumen. For example, as described in detail above, in certain embodiments, the one or more actions include causing a change in temperature applied to temperature-sensitive material in an inner wall, an outer wall, or one or more chambers of the device. In certain embodiments, the one or more actions include causing a change in a magnetic field applied to material in the inner wall, the outer wall, or one or more chambers of the device.

In certain embodiments, the one or more actions include changing an amount of material in at least one chamber of one or more chambers of the device. A change in the amount of material may be based on an estimated new volume of the lumen. For example, in certain embodiments, an airflow for the airway passage to prevent collapsing of the airway passage may be determined, and a new volume of the lumen corresponding to the determined airflow may be determined. These steps may be performed a certain period of time (or at multiple times) after the device has been positioned in the airway passage and/or after progression of one or more respiratory conditions of the patient.

In certain embodiments, the one or more actions include placing a deflated balloon within the lumen of the device. As such, the volume of the lumen may be changed by inflating the deflated balloon until at least a portion of the inflated balloon is in contact with the inner wall of the device thereby causing deformation of the inner wall of the device (and correspondingly, a change in the volume of the lumen).

In certain embodiments, the one or more actions include operating electronic circuitry. In particular, the device may include electronic circuity embedded between an outer wall and an inner wall. The electronic circuitry may be configured to receive control signals from an external stimulus and cause the inner wall of the device to narrow, or gradually toward a center of the lumen of the device. The electronic circuitry may be powered by a battery. The battery may be enclosed in the device. The electronic circuitry may also be powered using other known power sources.

In certain embodiments, a volume of the lumen may change until a targeted region is closed. In other words, changing the volume of the lumen may be used for gradual closure of the targeted region. This may be the treatment decision if the targeted lung region is severely affected with emphysema. During planning as part of patient treatment, a clinician may determine that a targeted region needs to eventually collapse or be closed. In such a case, a device, having an inner lumen capable of gradual narrowing over time, may be placed.

An example device may include a device with a one-way valve positioned within the lumen of the device. The one-way valve may allow for airflow, mucus, and/or other secretions to flow from a distal end of the lumen to a proximal end of the lumen (i.e. towards a patient's mouth). Further, the device may be configured to transition between (1) a first configuration where a gap exists between at least a portion of the one-way valve and the inner wall and (2) a second configuration where the gap no longer exists between the one-way valve and the inner wall. This device may allow for gradual and complete closure of the targeted region, while also continuing to allow air, mucus, and/or other secretions to continue to flow through the one-way valve (e.g., in one direction). The length of time between device placement and complete closure of the device's lumen (e.g., time between transitioning from the first configuration to the second configuration) may be several hours, several days, or several weeks. This approach may provide advantages over using EBVs. In particular, one-way EBVs are unidirectional in nature to prevent air from flowing further into the airways during inhalation, and allow air to flow outwards. The goal of an EBV is to release the air from hyperinflated regions of the lung in time, eventually leading to a collapsed, dysfunctional lung lobe. These EBV devices have valves embedded within that enable unidirectional flow, and no other opening is available. As such, the advantage of this approach, as compared to using EBVs is that the device described herein may gradually narrow the inflowing air passage and, in time, block air from flowing in through the airway. As a result, gradually more inhaled air may flow to neighboring lung regions which gives the lungs the time to adapt and accept the increased inflowing air without getting damaged-as opposed to a sudden large increase in inflowing air after EBV placement that often triggers pneumothorax as a complication.

In certain embodiments, the one-way valve in the inner lumen of the device is fixed in a mesh-like structure, or membrane, that contains openings to allow air to flow through, at one or more points within the lumen (e.g., air may flow in both directions). However, as the lumen is further narrowed over time after placement (e.g., in a predetermined timeframe based on qCT data during pre-treatment planning), this may result in complete closure of the mesh structure surrounding the one-way valve, such that air can only pass through the one-way valve in one direction (e.g., outward). This provides an alternative solution to BLVR, but with the reduced risk of pneumothorax as there is an increase in airflow to the surrounding lung lobes over time, allowing the neighboring lobes to adjust gradually, thereby reducing the overall pressure to the respiratory system to adjust immediately. Alternatively, a device may also be used in combination with any existing treatments such as EBV for reducing the risk of pneumothorax.

In certain embodiments, changing the volume of the lumen involves gradually widening a narrowed section of the inner lumen over a certain (predetermined) period of time. For example, inserting a deflated balloon into the device through flexible bronchoscopy and inflating the balloon may cause a narrowed section of the lumen to "dilate". In some cases, widening a narrow section may also help to gradually reduce the resistance to airflow in the airway passage. The device may be removed in a bronchoscopic procedure at the completion of the treatment.

In certain embodiments, changing the volume of the lumen involves changing the cross-sectional diameter equally of the lumen along the length of the lumen, such that the cross-sectional diameter of the lumen remains the same, or constant, along the length of the lumen. The device may then either be removed after the lung lobes surrounding the lobe treated with EBV have adapted to the increased airflow (i.e., at the completion of the treatment or may be replaced with another device with a different cross-sectional diameter of the inner lumen wherein the cross-sectional diameter of the inner lumen may be increased or decreased, as per the need).

It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the disclosure, which is defined in the accompanying claims. Further, it is too be understood that the methods, systems, and devices disclosed herein may be used in parts or in combination with other standard devices or methods.

It is to be understood that embodiments described herein are exemplary in nature and not limiting in any kind. Devices, methods and systems may be used in treatment for other conditions such as cardiac conditions or conditions that may involve treatment with stents or the like. A person skilled in the art may recognize that migration, mucus plugging, etc may be problematic in conditions other than respiratory as well.

What is claimed is:

1. A pulmonary implant device comprising:

an outer wall;

an inner wall defining a lumen from a proximal end to a distal end of the pulmonary implant device; and a one-way valve positioned within the lumen, the one-way valve configured to permit airflow in a first direction through the one-way valve and prevent airflow in a second direction through the one-way valve, wherein, in at least a first configuration of the pulmonary implant device, there is a gap between at least a portion of the one-way valve and the inner wall, the gap configured to permit airflow in both the first direction and the second direction through the lumen from the proximal end to the distal end of the pulmonary implant device.

2. The pulmonary implant device of claim 1, wherein, in a second configuration of the pulmonary implant device, there is no gap between the one-way valve and the inner wall, wherein the pulmonary implant device is configured to transition between the first configuration and the second configuration.

3. The pulmonary implant device of claim 2, wherein at least one of the inner wall and the outer wall comprises a material configured to transition the pulmonary implant device between the first configuration and the second configuration based on temperature.

4. The pulmonary implant device of claim 2, wherein at least one of the inner wall and the outer wall comprises a material configured to transition the pulmonary implant device between the first configuration and the second configuration based on a magnetic field.

5. The pulmonary implant device of claim 2, wherein at least one of the inner wall or the outer wall comprises a material configured to transition the pulmonary implant device between the first configuration and the second configuration based on an external pressure.

6. The pulmonary implant device of claim 2, further comprising electronic circuitry embedded between the outer wall and the inner wall configured to transition the pulmonary implant device between the first configuration and the second configuration.

7. The pulmonary implant device of claim 6, further comprising a battery coupled to the electronic circuitry and positioned between the outer wall and the inner wall.

8. The pulmonary implant device of claim 1, further comprising: one or more chambers formed between the outer wall and the inner wall.

9. The pulmonary implant device of claim 8, wherein the one or more chambers, when at least partially filled with material, are configured to transition the pulmonary implant device to a second configuration without the gap between the one-way valve and the inner wall.

10. The pulmonary implant device of claim 8, wherein the one or more chambers comprise a first chamber coupled to a first fluid path through the outer wall and a second chamber coupled to a second fluid path through the outer wall, the first fluid path being separate from the second fluid path.

11. The pulmonary implant device of claim 1, wherein the inner wall is at least partially coated with a coating material comprising at least one of hydrophobic characteristics or hydrophilic characteristics.

12. The pulmonary implant device of claim 11, wherein the coating material comprises at least one of platinum modified fibrous carbon mesh or polymers.

13. The pulmonary implant device of claim 12, wherein the coating material comprises one or more biomolecules.

14. The pulmonary implant device of claim 13, wherein the one or more biomolecules comprise polyethylene glycol (PEG).

15. The pulmonary implant device of claim 11, wherein a concentration of the coating material on the inner wall decreases along a length of the lumen from the distal end to the proximal end of the pulmonary implant device.

16. The pulmonary implant device of claim 1, further comprising a mesh structure coupling the one-way valve to the inner wall.

17. The pulmonary implant device of claim 1, wherein the outer wall is shaped to fit within an airway within a lung of a respiratory system.

18. The pulmonary implant device of claim 17, wherein a surface of the outer wall is contoured to conform to a pulmonary region of a single specific patient.

19. The pulmonary implant device of claim 1, wherein the outer wall comprises an outer surface having at least one of: raised portions, protrusions, or embossed portions.

* * * * *